(12) United States Patent
Mori et al.

(10) Patent No.: US 8,105,431 B2
(45) Date of Patent: Jan. 31, 2012

(54) SUBPHTHALOCYANINE DERIVATIVE HAVING PHOSPHORUS DERIVATIVE AS AXIALLY SUBSTITUTED GROUP, METHOD FOR MANUFACTURING THE SAME AND OPTICAL FILM USING THE SAME

(75) Inventors: Tomohiro Mori, Neyagawa (JP); Yasuhiro Yamasaki, Neyagawa (JP)

(73) Assignee: Orient Chemical Industries, Ltd., Osaka (JP)

( * ) Notice: Subject to any disclaimer, the term of this patent is extended or adjusted under 35 U.S.C. 154(b) by 404 days.

(21) Appl. No.: 12/461,369

(22) Filed: Aug. 10, 2009

(65) Prior Publication Data

US 2010/0036134 A1 Feb. 11, 2010

(30) Foreign Application Priority Data

Aug. 8, 2008 (JP) ................. 2008-206016

(51) Int. Cl.
*C07F 5/02* (2006.01)
(52) U.S. Cl. .................... 106/287.2; 548/405
(58) Field of Classification Search ............... 106/287.2; 548/405
See application file for complete search history.

(56) References Cited

U.S. PATENT DOCUMENTS

2008/0210128 A1* 9/2008 Mori et al. ............ 106/287.2

FOREIGN PATENT DOCUMENTS

| JP | A-8-64492 | 3/1996 |
|----|-----------|--------|
| JP | A-10-330633 | 12/1998 |
| JP | A-11-024255 | 1/1999 |
| JP | A-2004-10838 | 1/2004 |
| JP | A-2005-200601 | 7/2005 |
| JP | A-2005-289854 | 10/2005 |
| JP | A-2005-344021 | 12/2005 |
| JP | A-2006-13226 | 1/2006 |
| JP | A-2007-139959 | 6/2007 |
| JP | A-2008-216589 | 9/2008 |

OTHER PUBLICATIONS

European Search Report issued in European Patent Application No. 09167252.7 on May 12, 2010.

* cited by examiner

*Primary Examiner* — Joseph Kosack
(74) *Attorney, Agent, or Firm* — Oliff & Berridge, PLC

(57) ABSTRACT

A novel subphthalocyanine derivative having a phosphorus derivative-substituted group as an axially substituted group which has an excellent solubility, a method for producing the same and an optical film containing the same, are provided without impairing excellent properties peculiar to the original subphthalocyanines. The novel subphthalocyanine derivative is represented by the following chemical formula (1), and it is applicable for optical films.

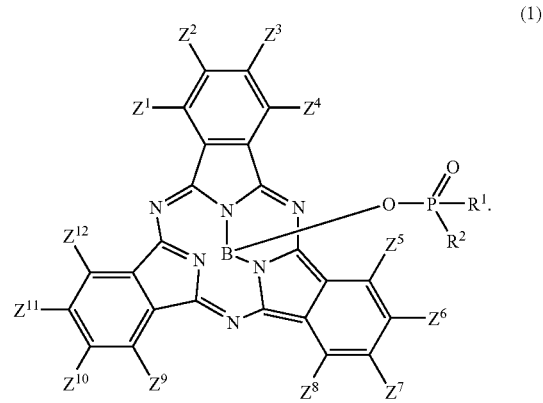

(1)

3 Claims, 2 Drawing Sheets

SUBPHTHALOCYANINE DERIVATIVE HAVING PHOSPHORUS DERIVATIVE AS AXIALLY SUBSTITUTED GROUP, METHOD FOR MANUFACTURING THE SAME AND OPTICAL FILM USING THE SAME

TECHNICAL FIELD

The present invention relates to a novel subphthalocyanine derivative having a phosphorus derivative as an axially substituted group, a method for manufacturing the same, and an optical film using the same.

BACKGROUND OF THE INVENTION

Optical films which are functional optical thin films used for, for example, light-transmissive films such as antireflection films, color filters, optical filters etc., are important and indispensable elements for displaying clear images on image display devices such as liquid crystal devices or plasma display devises.

Almost all such optical films have been prepared from inorganic compounds by film forming methods such as a chemical vapor deposition (CVD) method or a physical vapor deposition (PVD) method. Examples using organic compounds have also been reported. For example, in Japanese Patent Publication No. 08-64492A, antireflection films prepared from metal-free phthalocyanines are disclosed.

It has been also known that functional optical thin films, optical elements and their raw materials can be manufactured from subphthalocyanines which are ring-contracted forms of phthalocyanines. For example, Japanese Patent Publication No. 2004-10838A discloses color resist inks and color filters used for emitting blue color. An aqueous blue ink for full-color printing of high bright colorfulness is disclosed in Japanese Patent Publication No. 2005-200601A, and a colorant that absorbs orange color light used for front panels of plasma display devices is disclosed in Japanese Patent Publication No. 2006-13226A. In addition, light-emitting devices using organic light-emitting diodes (LEDs) are disclosed in Japanese Patent Publication No. 2005-344021A.

Subphthalocyanines have been studied in an effort to apply them to various industrial fields such as pigment, thin film chemical materials, information recording materials, light emitting materials, etc.

However, subphthalocyanines of pigment have poor light resistance and poor solubility. Therefore, when thin films are required, it is necessary to prepare a pigment-dispersed liquid by dispersing the subphthalocyanines into a solvent and then apply the liquid to form a thin film. The thus obtained thin film made from such pigment-dispersed liquid cannot achieve sufficient transparency unless the subphthalocyanines are pulverized into an ultrafine homogeneous particle size of not more than 0.5 μm and with a very narrow particle size distribution. However, when the subphthalocyanines are pulverized into the ultrafine particle size region, the surface area thereof increases, causing further deterioration in light resistance. Furthermore, it is difficult to prepare homogeneous thin films if a liquid which contains a hardly dispersible pigment is used.

On the other hand, optical films such as functional optical thin films having light absorptivity in a specific wavelength region, antireflection films especially coated on marketable wide screen display panels such as plasma display panels (PDP) or liquid crystal display panels, color filters, optical recording media for using light of blue laser region, photoreceptors etc. are required to have a small half width in 530-580 nm of wavelength and also a sufficient light absorption properties.

SUMMARY OF THE INVENTION

The present invention has been developed to solve such problems mentioned above and an object of the present invention is to provide a novel subphthalocyanine derivative having a phosphorus derivative substituted-group as an axially substituted group, which is excellent in solubility, without damaging unique properties peculiar to original subphthalocyanines and also to provide a method for manufacturing the same.

Another object of the present invention is to provide excellent optical films which are capable to be used as the functional optical thin films, have resistance to light and heat and have light absorptivity in a specific wavelength region, by using the subphthalocyanine derivative having the phosphorus derivative-substituted group.

The subphthalocyanine derivative having the phosphorus derivative-substituted group which has a phosphorous derivative-substituted group as an axially substituted group (i.e. a boron subphthalocyanine derivative having the phosphorus derivative-substituted group) of the present invention developed for accomplishing the foregoing objects is represented by the following chemical formula (1):

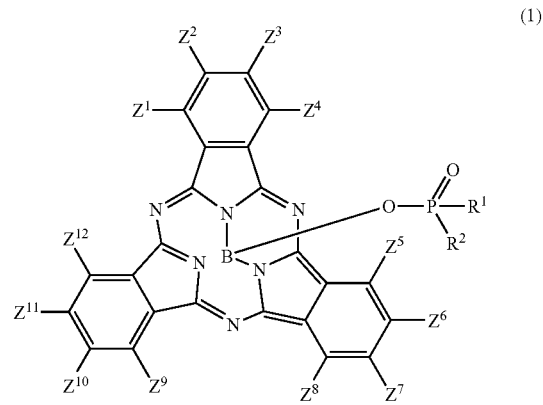

(In the chemical formula (1), $Z^1$-$Z^{12}$ are the same or different from each other and each represents a hydrogen atom, a hydroxyl group, a mercapto group, an alkyl containing group, a partial fluoro alkyl containing group, a perfluoro alkyl containing group, an aralkyl containing group, a partial fluoro aralkyl containing group, a perfluoro aralkyl containing group, an aryl group, an amino group, an alkoxyl group or a thioether group. $R^1$ and $R^2$ are the same or different from each other and each represents an alkyl group, an aralkyl group, a phenyl group, an alkoxyl group or a phenoxy group.)

The method for manufacturing the subphthalocyanine derivative having the phosphorus derivative-substituted group comprises;

a step for reacting a halo boron subphthalocyanine represented by the following chemical formula (2):

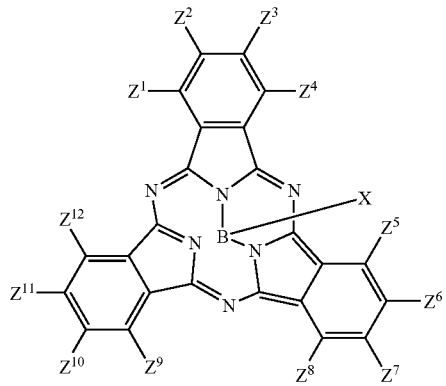

(2)

(In the chemical formula (2), $Z^1$-$Z^{12}$ are the same as described in the aforementioned formula (1). X is a halogen atom selected from the group consisting of fluorine, chlorine, bromine and iodine.)

with a compound represented by the following chemical formula (3):

$$R^1R^2PO_2H \quad (3)$$

(wherein $R^1$ and $R^2$ are the same or different from each other and are each selected from the group consisting of a straight or branched alkyl group having 1-20 carbon atoms, an aralkyl group, a phenyl group, an alkoxyl group and a phenoxy group, each of which no substituent or one or more substituents)

to manufacture the subphthalocyanine derivative having the phosphorus derivative-substituted group as an axially substituted group represented by the following chemical formula (1):

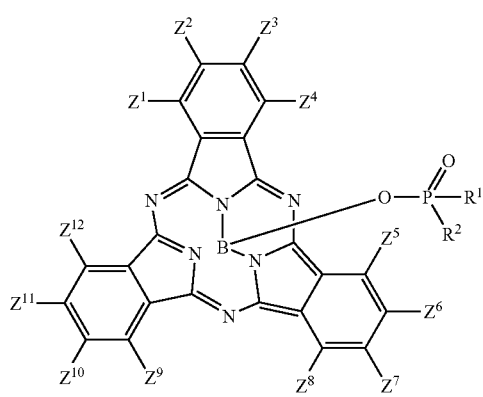

(1)

(wherein $Z^1$-$Z^{12}$, $R^1$ and $R^2$ are the same as described above.)

The optical film contains the subphthalocyanine derivative having the phosphorus derivative-substituted group.

DETAILED EXPLANATION OF THE INVENTION

Figure 1:
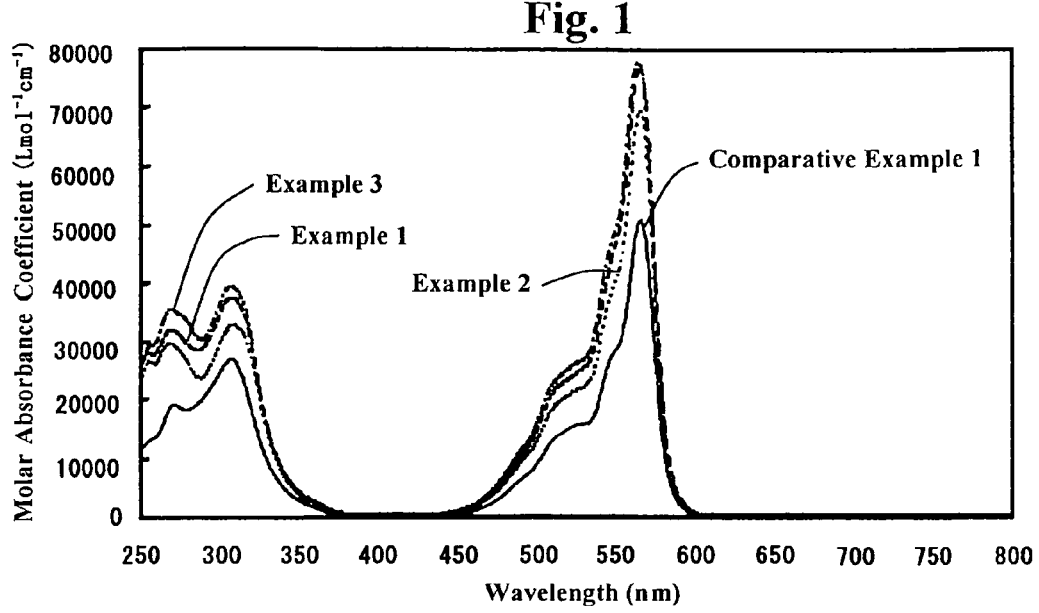
FIG. 1 shows absorption spectra of subphthalocyanine derivatives having no peripheral substituent of Examples 1-3 and a Comparative Example 1.

The subphthalocyanine derivative having a phosphorus derivative-substituted group which has a phosphorus derivative substituted-group as an axially substituted group has an excellent light resistance and heat resistance, high solubility to various solvents, absorption band of small half width in 530-590 nm wavelength in visible light region and high absorption coefficient. Compared to the halo boron subphthalocyanine, shift in a required wavelength and broadening in the half width due to molecular association in a solid state (i.e. in a state of thin film) can be remarkably suppressed when the subphthalocyanine derivative having the phosphorus derivative-substituted group is used.

In addition, the subphthalocyanine derivative having the phosphorus derivative-substituted group as the axially substituted group can be manufactured easily on a large scale and in high yield, by a reaction of the halo boron subphthalcyanines with corresponding phosphorus derivatives.

Further, the optical film containing the present subphthalocyanine derivative having the phosphorus derivative-substituted group as an axially substituted group can be formed into a homogeneous thickness film by applying the subphthalocyanine-dispersed liquid because the present subphthalocyanine derivatives having the phosphorus derivative-substituted group have high solubility to solvents. Further, thus obtained optical film contains the subphthalocyanine derivatives having the phosphorus derivative-substituted group which has an excellent light resistance and heat resistance, so the optical film has an excellent toughness. Furthermore, the optical film has an absorption band of a small half width in 530-590 nm wavelength in the visible light region so that light having a specific wavelength can be selectively blocked.

Therefore, display devices etc. coated by the optical film produce clear images with high contrast ratio. The optical film such as an antireflection thin film or a light-transmissive thin film has properties to selectively absorb light in a wavelength of 510-610 nm, orange color light (550-620 nm) and light at the center of the human visual sensitivity (560 nm), which deteriorate the clearness of images on the display devices. However, the optical film does not disturb to absorb other visible light regions, accordingly, the film is extremely useful for improving visibility of images on display devices.

Preferred embodiments of the present invention are described below, but it is noted that the scope of the present invention is not limited to these embodiments. The present subphthalocyanine derivative having the phosphorus derivative-substituted group is represented by the aforementioned chemical formula (1).

The subphthalocyanine derivatives having the phosphorus derivative-substituted group can also be represented, for example, by the following chemical formula (4):

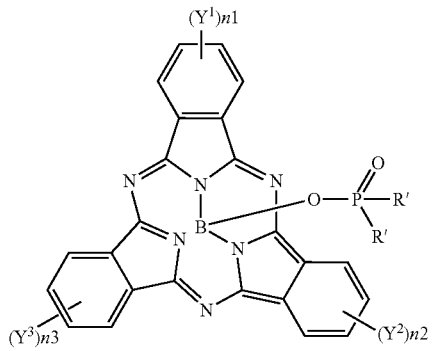

(4)

(In the chemical formula (4), $Y^1$-$Y^3$ are the same or different from each other and each represents a hydrogen atom; hydroxyl group; mercapto group;

an unsubstituted-, partial fluoro-substituted-, perfluoro-substituted- or substituent-containing-alkyl group having a straight or branched chain of 1-20 carbon atoms;

an unsubstituted-, partial fluoro-substituted-, perfluoro-substituted- or substituent-containing-aralkyl group having a straight or branched chain of 1-20 carbon atoms; or an unsubstituted- or substituent-containing-group selected from the group consisting of an aryl group, an amino group, an alkoxyl group, a phenoxy group and a thioether group.

n1-n3 are the same or different from each other and are each represents an integer ranging from 1 to 4.

R' groups are the same or different from each other and each is an unsbstituted- or substituent-containing-group selected from the group consisting of a straight or branched chain of alkyl group having 1-20 carbon atoms, an aralkyl group, an aryl group, an alkoxyl group and a phenoxy group.)

In the foregoing chemical formula, as concrete examples of the substituted group of $Y^1$-$Y^3$, following substituted groups can be exemplified. However, it is noted that the substituted group that the present subphthalocyanine derivatives can have, are not limited to these substituted groups.

As an unsubstituted alkyl group, methyl group, ethyl group, n-propyl group, i-propyl group, n-butyl group, i-butyl group, sec-butyl group, t-butyl group, n-pentyl group, neo-pentyl group, n-hexyl group, n-heptyl group, n-octyl group, 2-ethylhexyl group, n-decyl group, lauryl group, stearyl group etc, can be exemplified.

As a partial fluoro-substituted alkyl group, 2,2,2-trifluoroethyl group, 3,3,3-trifluoropropyl group, 2,2,3,3,3-pentafluoropropyl group, 4,4,4-trifluorobutyl group can be exemplified.

Further, as a perfluoro-substituted alkyl group, perfluoromethyl group, perfluoroethyl group, perfluoro-n-propyl group, perfluoro-i-propyl group, perfluoro-n-butyl group, perfluoro-1-butyl group, perfluoro-sec-butyl group, perfluoro-n-pentyl group, perfluoro-neo-pentyl group, perfluoro-n-hexyl group, perfluoro-n-heptyl group, perfluoro-n-octyl group, perfluoro-n-decyl group etc. can be exemplified.

As an unsubstituted aralkyl group, benzyl group, •,•-dimethylbenzyl group etc. can be exemplified.

As a partial fluoro-substituted aralkyl group, —$CF_2C_6H_5$ group, —$C(CF_3)_2C_6H_5$ group etc. can be exemplified. As a perfluoro-substituted aralkyl group, —$CF_2C_6F_5$ group, —$C(CF_3)_2C_6F_5$ group etc. can be exemplified.

As an aryl group, a phenyl group, a naphthyl group etc. can be exemplified.

As an amino group, amino group; a monoalkylamino group such as methylamino group, ethylamino group, n-propylamino group, i-propylamino group, n-butylamino group, sec-butylamino group, t-butylamino group, n-pentylamino group, neo-pentylamino group, n-hexylamino group, n-heptylamino group, n-octylamino group etc.; a dialkylamino group such as dimethylamino group, diethylamino group, di-n-propylamino group, di-i-propylamino group, di-n-butylamino group, di-sec-butylamino group, di-t-butylamino group, di-n-pentylamino group, di-neo-pentylamino group, di-n-hexylamino group, di-n-heptylamino group, di-n-octylamino group etc. can be exemplified.

As an alkoxyl group, methoxy group, ethoxy group, n-propoxy group, i-propoxy group, n-butoxy group, i-butoxy group, sec-butoxy group, t-butoxy group, n-pentyloxy group, neo-pentyloxy group, n-hexyloxy group, n-heptyloxy group, n-octyloxy group etc. can be exemplified.

As a thioether group, methylthio group, ethylthio group, n-propylthio group, i-propylthio group, n-butylthio group, i-butylthio group, sec-butylthio group, t-butylthio group, n-pentylthio group, neo-pentylthio group, n-hexylthio group, n-heptylthio group, n-octylthio group, phenylthio group, naphthylthio group etc. can be exemplified.

Each of these above-mentioned groups may have another substituted group. As the another substituted group, a halogen group such as F, Cl, Br, I etc.; nitro group; cyano group; hydroxyl group; mercapto group; an alkyl group such as methyl group, ethyl group, propyl group, butyl group, pentyl group, hexyl group, 2-ethylhexyl group, n-octyl group etc.; an alkoxyl group such as methoxy group, ethoxy group, propoxy group, butoxy group, pentyloxy group, hexyloxy group, 2-ethylhexyloxy group, n-octyloxy group etc.;

an aryl group such as phenyl group, naphthyl group, phenethyl group etc.; an aralkyl group such as benzyl group, •,•-dimethylbenzyl group etc.; amino group; an alkylamino group; a dialkylamino group etc. can be exemplified.

In the foregoing chemical formula (4), as an example of the substituted group of R', following substituted group can be exemplified. However, it is noted that the subphthalocyanine derivatives having the phosphorus derivative-substituted group are not limited to these substituted groups.

As an alkyl group, methyl group, ethyl group, n-propyl group, i-propyl group, n-butyl group, i-butyl group, sec-butyl group, t-butyl group, n-pentyl group, neo-pentyl group, n-hexyl group, n-heptyl group, n-octyl group, 2-ethylhexyl group, n-decyl group, lauryl group, stearyl group etc. can be exemplified.

As an aralkyl group, benzyl group, •,•-dimethylbenzyl group etc. can be exemplified.

As an aryl group, phenyl group, naphthyl group etc. can be exemplified.

As an alkoxyl group, methoxy group, ethoxy group, n-propoxy group, i-propoxy group, n-butoxy group, sec-butoxy group, t-butoxy group, n-pentyloxy group, neo-pentyloxy group, n-hexyloxy group, n-heptyloxy group, n-octyloxy group etc. can be exemplified.

Each of these above-mentioned groups may have another substituted group.

As the another substituted group, a halogen group such as F, Cl, Br, I etc.; a nitro group; cyano group; hydroxyl group; mercapto group; an alkyl group such as methyl group, ethyl group, propyl group, butyl group, pentyl group, hexyl group, 2-ethylhexyl group, n-octyl group etc.; an alkoxyl group such as methoxy group, ethoxy group, propoxy group, butoxy group, pentyloxy group, hexyloxy group, 2-ethylhexyloxy group, n-octyloxy group etc.;

an aryl group such as phenyl group, naphthyl group, phenethyl group etc.; an aralkyl group such as benzyl group, •,•-dimethylbenzyl group etc.; amino group; an alkylamino group; a dialkylamino group etc. can be exemplified.

The present subphthalocyanine derivatives having the phosphorus derivative-substituted group can be obtained by the following process.

The subphthalocyanine derivatives having the phosphorus derivative-substituted group can be manufactured by a reaction of a halo boron subphthalocyanine with a phosphorus derivative. By using this process, the subphthalocyanine derivatives having the phosphorus derivative-substituted group can be obtained simply in high yield. The subphthalocyanine derivatives having the phosphorus derivative-substituted group are excellent in solubility in solvents and excellent in resistance to light and heat so that they can be used for various technical fields such as for inks, functional optical thin films etc.

A precise process for manufacturing the subphthalocyanine derivatives having the phosphorus derivative-substituted group is shown below.

A halo boron subphthalocyanine can be synthesized by a reaction of phthalonitrile derivative with a boron trihalide in a way as disclosed in Japanese Patent Publication No. 2005-289854A or Japanese Patent Application No. 2007-053265 or in a similar way A chemical reaction formula thereof is represented by the following reaction formula (5):

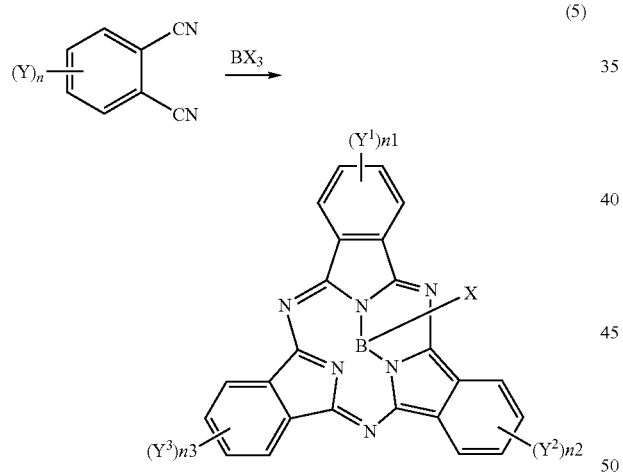

(In the chemical formula (5), Y and $Y^1$-$Y^3$ are the same or different from each other and each represents a hydrogen atom; hydroxyl group; mercapto group; an unsubstituted-, partial fluoro-substituted-, perfluoro-substituted- or substituent-containing-alkyl group having a straight or branched chain of 1-20 carbon atoms; an unsubstituted-, partial fluoro-substituted-, perfluoro-substituted- or substituent-containing-aralkyl group having a straight- or branched-chain of 1-20 carbon atoms; or an unsubstituted- or substituent-containing-group selected from the group consisting of an aryl group, an amino group, an alkoxyl group, a phenoxy group and a thioether group.

n1-n3 are the same or different from each other and are each represents an integer ranging from 1 to 4.

R' groups are the same or different from each other and each is an unsubstituted- or substituent-containing-group selected from the group consisting of a straight or branched chain of alkyl group having 1-20 carbon atoms, an aralkyl group, an aryl group, an alkoxyl group and a phenoxy group.)

In the boron compound $BX_3$, X is a halogen atom such as fluorine, chlorine, bromine, iodine etc. Boron trichloride that has chlorine atoms as X is preferably used. This boron trichloride is in a state of gas at a room temperature and under a normal pressure, so the gas may be directly bubbled into a reaction mixture or may be dissolved into a solvent and then the boron trichloride-containing solution can be added into a reaction mixture dropwise, or the gas can be cooled down to be liquefied by an appropriate cooling means and then the liquefied boron trichloride can be dripped into the reaction mixture.

As a solvent for the synthesis reaction of the halo boron subphthalocyanine, the solvent is not particularly limited as long as the solvent has a high boiling point, has a good solubility to the phthalonitride derivatives and does not react with the boron halogenide. Examples of the solvent are toluene, xylene, mesitylene, monochlorobenzene, dichlorobenzene, trichlorobenzene, naphthalene, monomethylnaphthalene, monochloronaphthalene, dichloronaphthalene, quinoline, isoquinoline, sulfolane etc. These kinds of solvent can be used solely or in a mixture of two or more.

As shown in the following chemical reaction formula (6):

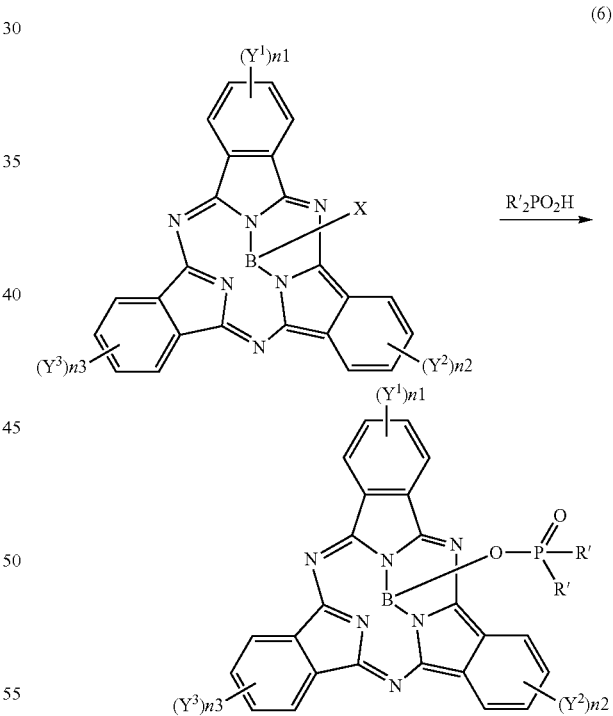

(in the chemical formula (6), $Y^1$-$Y^3$, n1-n3, X and R' are the same as previously described,)

the subphthalocyanine derivative having the phosphorus derivative-substituted group is obtained from the resulting halo boron subphthalocyanine through an axially-substituted-group exchange reaction with a phosphorus derivative.

The exchange reaction of the axially substituted group is more precisely explained below.

The subphthalocyanine derivatives having the phosphorus derivative-substituted group are synthesized through the axially-substituted-group exchange reaction by dissolving or suspending a halo boron subphthalocyanine and a phosphorus derivative in a solvent and then heating the solution or suspension in the presence of an appropriate base, if necessary, to induce the substitution reaction which is accompanied by dehydrohalogenation reaction.

Solvent that can be used for the axially-substituted-group exchange reaction is not specifically limited as long as the solvent dissolves or suspends the halo boron subphthalocyanine and the phosphorus derivative. As the solvent benzene, an alkyl benzene such as toluen, xylene, mesitylene, ethylbenzene, n-propylbenzene, cumene etc.; a halogenated benzene such as monochlorobenzene, dichlorobenzene, bromobenzene, dibromobenzene etc.; a nitrogen-containing solvent such as N,N-dimethylformamide, N,N-dimethylacetamide, N-methylpyrrolidone, 1,3-dimethyl-2-imidazolidinone, 1,3-dimethylpropylene urea etc.; an ether such as tetrahydrofuran, diphenyl ether, anisole, 1,4-dioxane, monoglyme, diglyme, triglyme etc.; and a ketone such as acetone, methyl ethyl ketone, methyl isobutyl ketone, cyclohexanone etc.; can be exemplified.

In the axially-substituted-group exchange reaction, an appropriate base may be used for eliminating by-product hydrogen halide to promote the reaction.

The base is not particularly limited as long as the base does not exert a bad influence on the groups in the halo boron subphthalocyanine or the phosphorus derivative. A hydroxide of alkali metal and alkali earth metal such as lithium hydroxide, sodium hydroxide, potassium hydroxide, calcium hydroxide etc.; a carbonate and a hydrogen carbonate such as lithium carbonate, sodium carbonate, potassium carbonate, cesium carbonate, calcium carbonate, sodium hydrogen carbonate, potassium hydrogen carbonate etc. can be exemplified.

The exchange reaction is carried out preferably at a reflux temperature of the solvent. And the reaction time thereof is ranging from 1 to 24 hours.

After the axially-substituted-group exchange reaction, the reaction mixture is preferably filtered to obtain the subphthalocyanine derivative having the phosphorus derivative-substituted group. Additionally, purification may be done to meet purpose of use.

The purification procedures, for example, column chromatography or recrystallization etc. can be used to obtain the reaction products. Other purification procedures may also be adopted.

Chemical structures of the halo boron subphthalocyanines are shown below as the intermediate compounds (1-20). "Bn" in the structures represents a benzyl group. It is noted that the halo boron subphthalocyanine is not limited to these structures.

Intermediate Compound 1

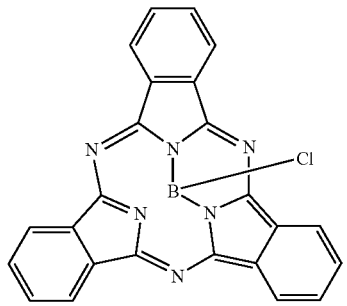

Intermediate Compound 2

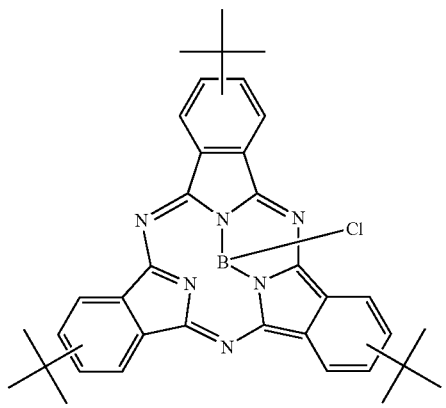

Intermediate Compound 3

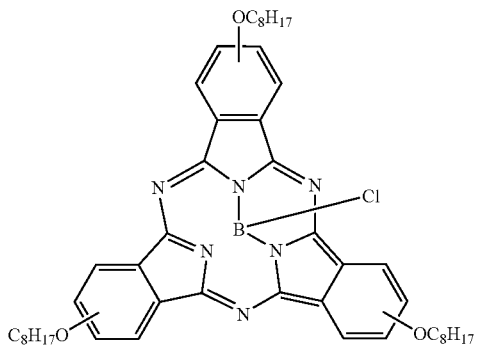

Intermediate Compound 4

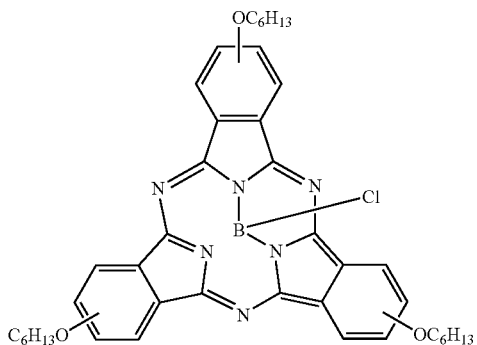

Intermediate Compound 5

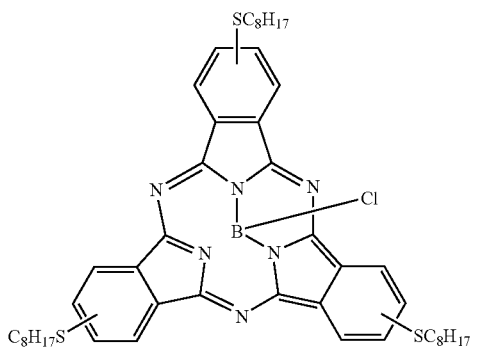

Intermediate Compound 6
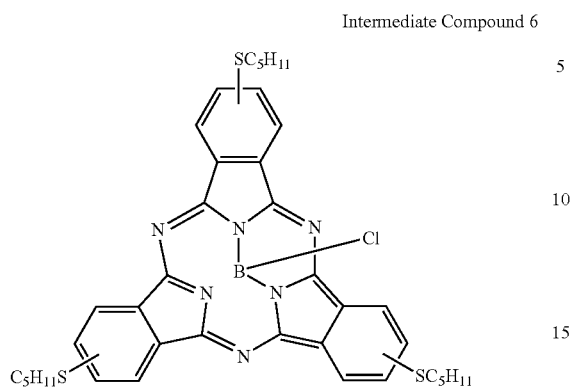
Intermediate Compound 7
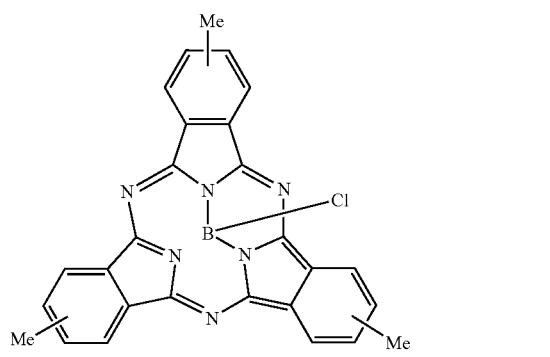
Intermediate Compound 8
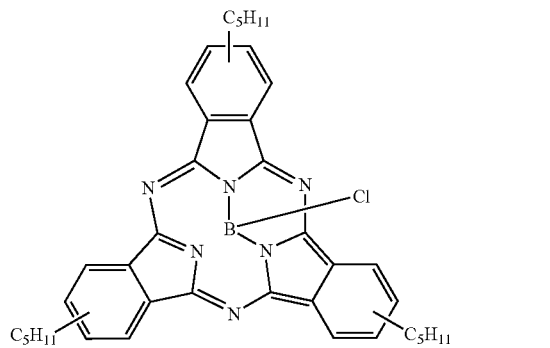
Intermediate Compound 9
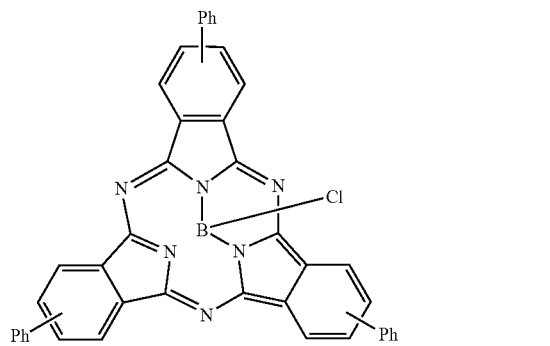
Intermediate Compound 10
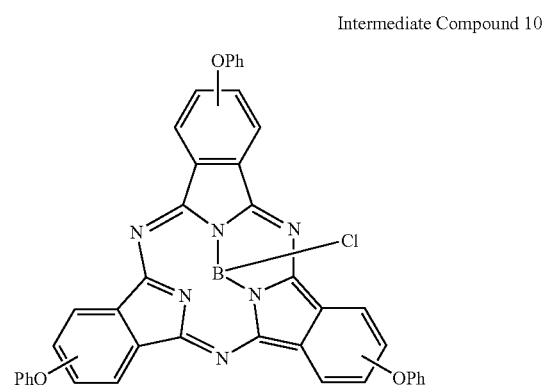
Intermediate Compound 11
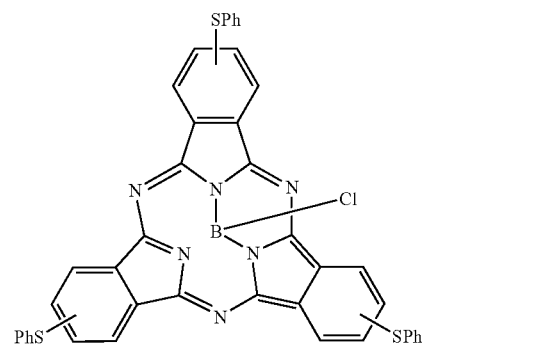
Intermediate Compound 12
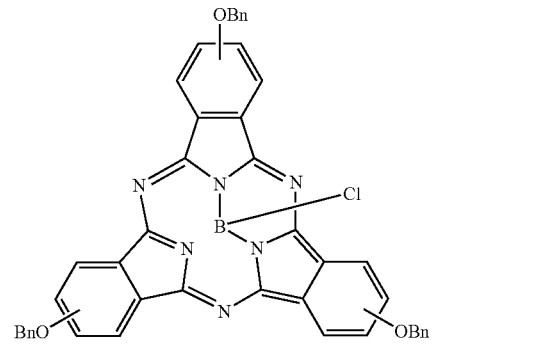
Intermediate Compound 13
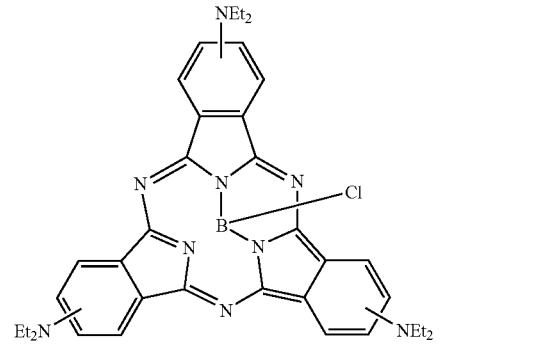

Intermediate Compound 14
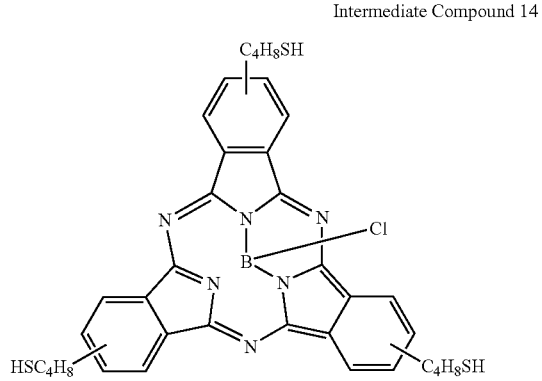

Intermediate Compound 15
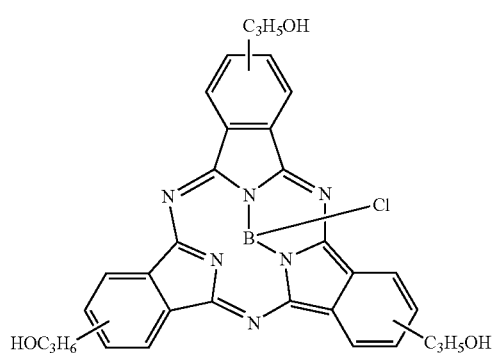

Intermediate Compound 16
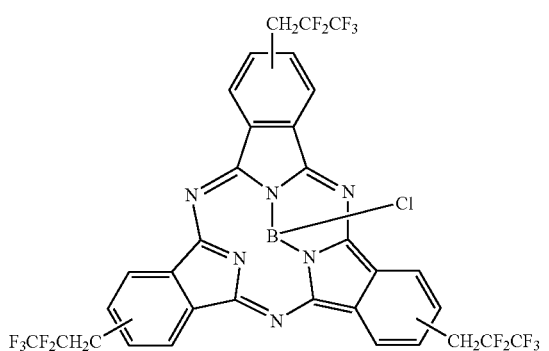

Intermediate Compound 17
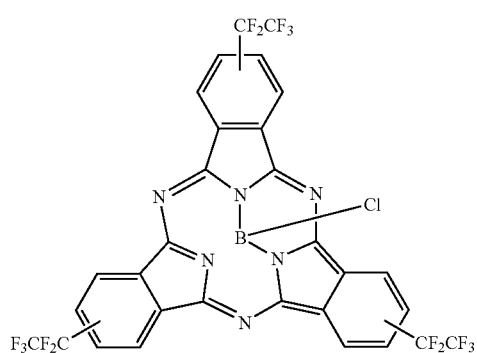

Intermediate Compound 18
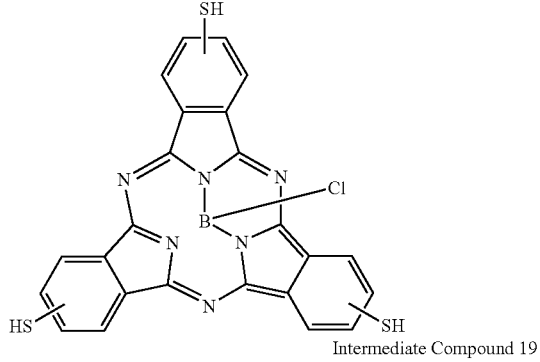

Intermediate Compound 19
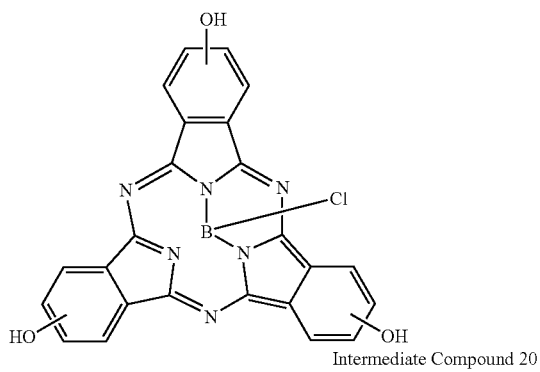

Intermediate Compound 20
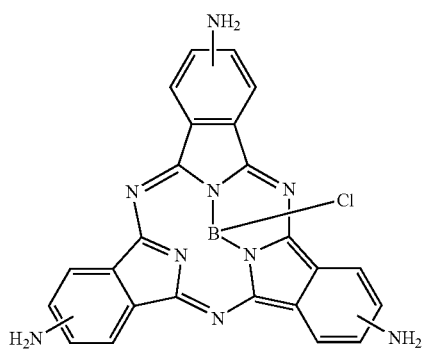

The phosphorus derivatives that can be used in the present invention are represented by the following formula (7).

$R'_2PO_2H$ (7)

(R' is the same as previously described.)

As concrete examples of the phosphorus derivative, a phosphinic acid derivative such as dimethylphosphinic acid, diethylphosphinic acid, di-n-propylphosphinic acid, di-n-butylphosphinic acid, di-sec-butylphosphinic acid, di-n-pentylphosphinic acid, di-n-hexylphosphinic acid, di-n-stearylphosphinic acid, diallylphosphinic acid, diphenylphosphinic acid, dibenzylphosphinic acid, dichloromethylphosphinic acid, di(2-methoxyethyl) phosphinic acid, ditolylphosphinic acid, dixylylphosphinic acid etc.; and a phosphoric acid derivative such as dimethylphosphoric acid, diethylphosphoric acid, di-n-propylphosphoric acid, di-n-butylphosphoric acid, di-sec-butylphosphoric acid, di-n-pentylphosphoric acid, di-n-hexylphosphoric acid, di-n-stearylphosphoric acid, diallylphosphoric acid, diphenylphosphoric acid, dibenzylphosphoric acid, dichloromethylphosophoric acid, di(2-methoxyethyl) phosphoric acid, ditolylphosphoric acid, dixylylphosphoric acid etc.; can be exemplified. It is noted that in the present invention the phosphorus derivative is not limited to the above-mentioned derivatives.

Chemical structures of the present subphthalocyanine derivatives having the phosphorus derivative-substituted group are shown below (Compounds 1-44). In the structures, "Bn" represents a benzyl group. It is noted that present subphthalocyanine derivatives having the phosphorus derivative-substituted group are not limited to these structures.

Compound 1

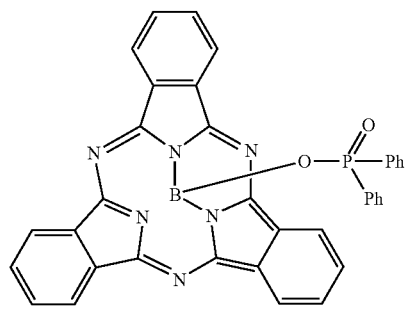

Compound 2

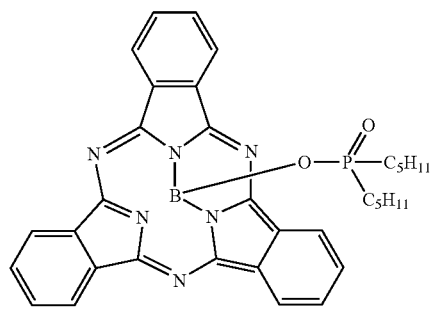

Compound 3

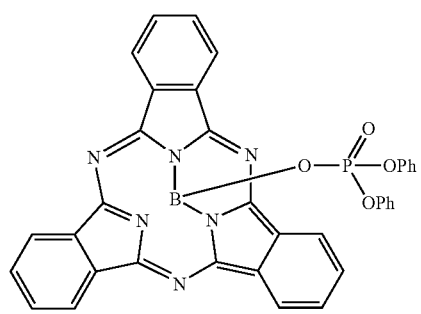

Compound 4

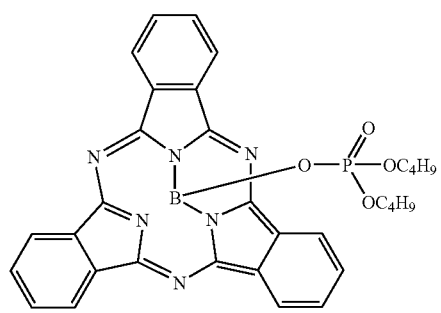

-continued

Compound 5

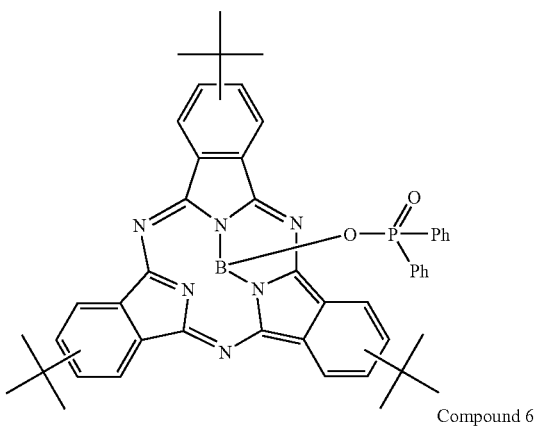

Compound 6

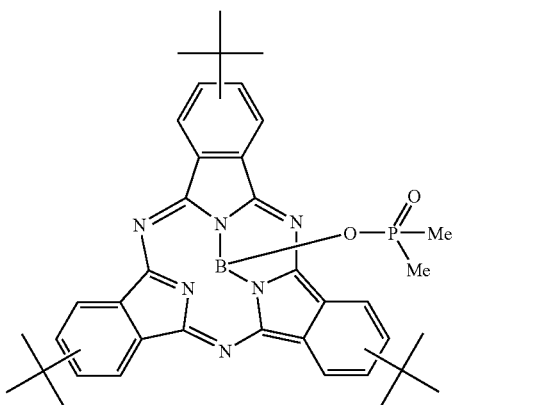

Compound 7

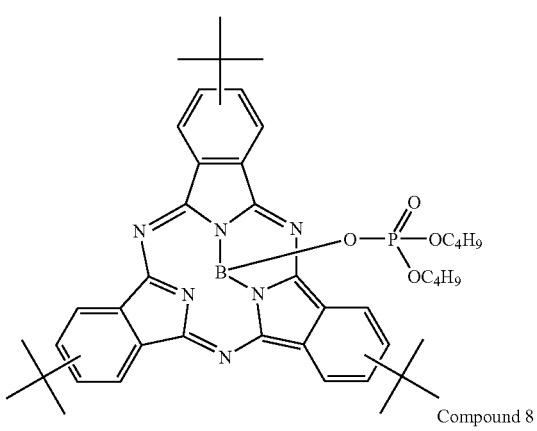

Compound 8

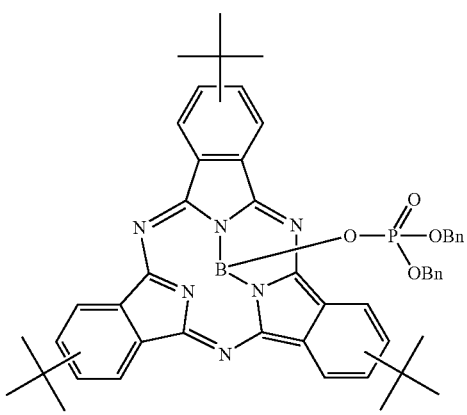

Compound 9
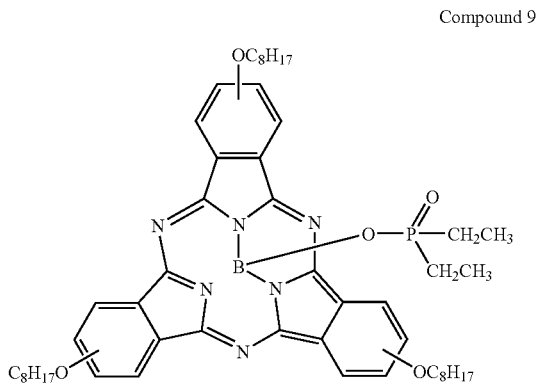
Compound 13
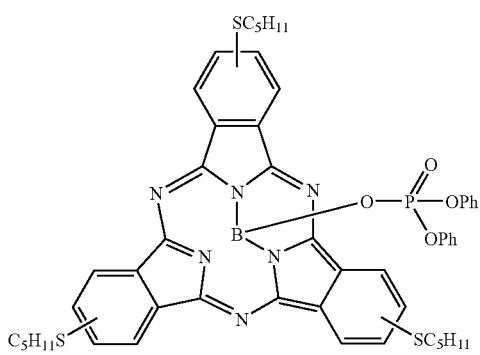
Compound 10
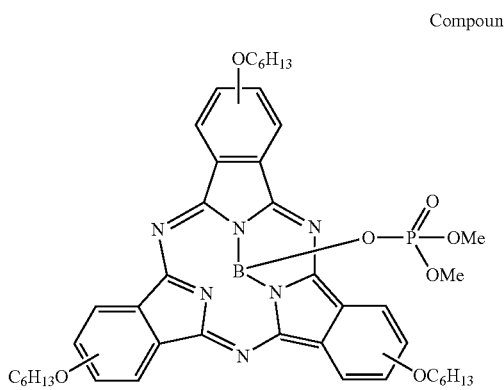
Compound 14
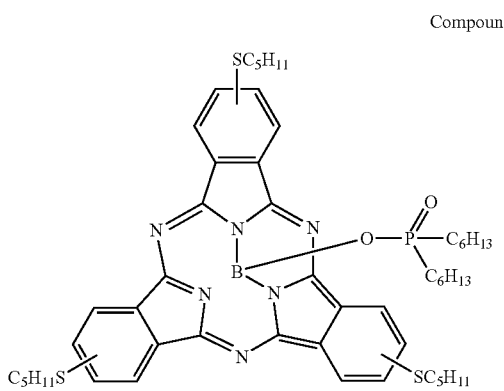
Compound 11
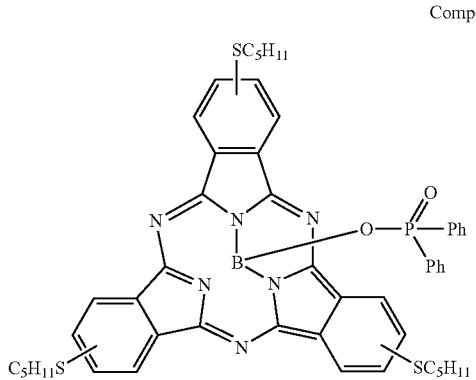
Compound 15
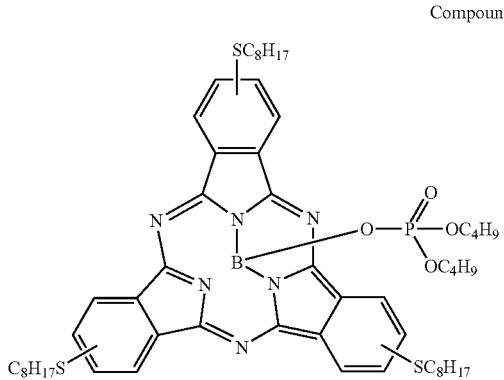
Compound 12
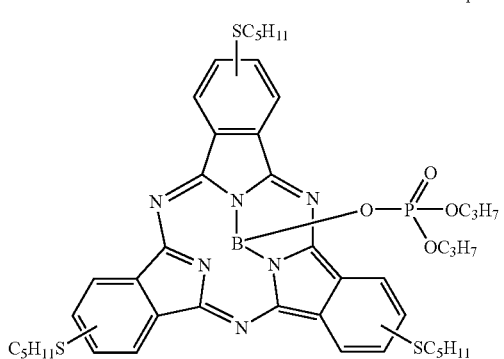
Compound 16
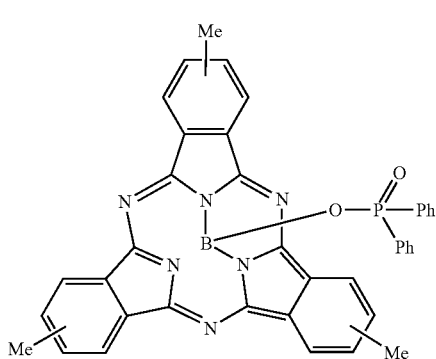

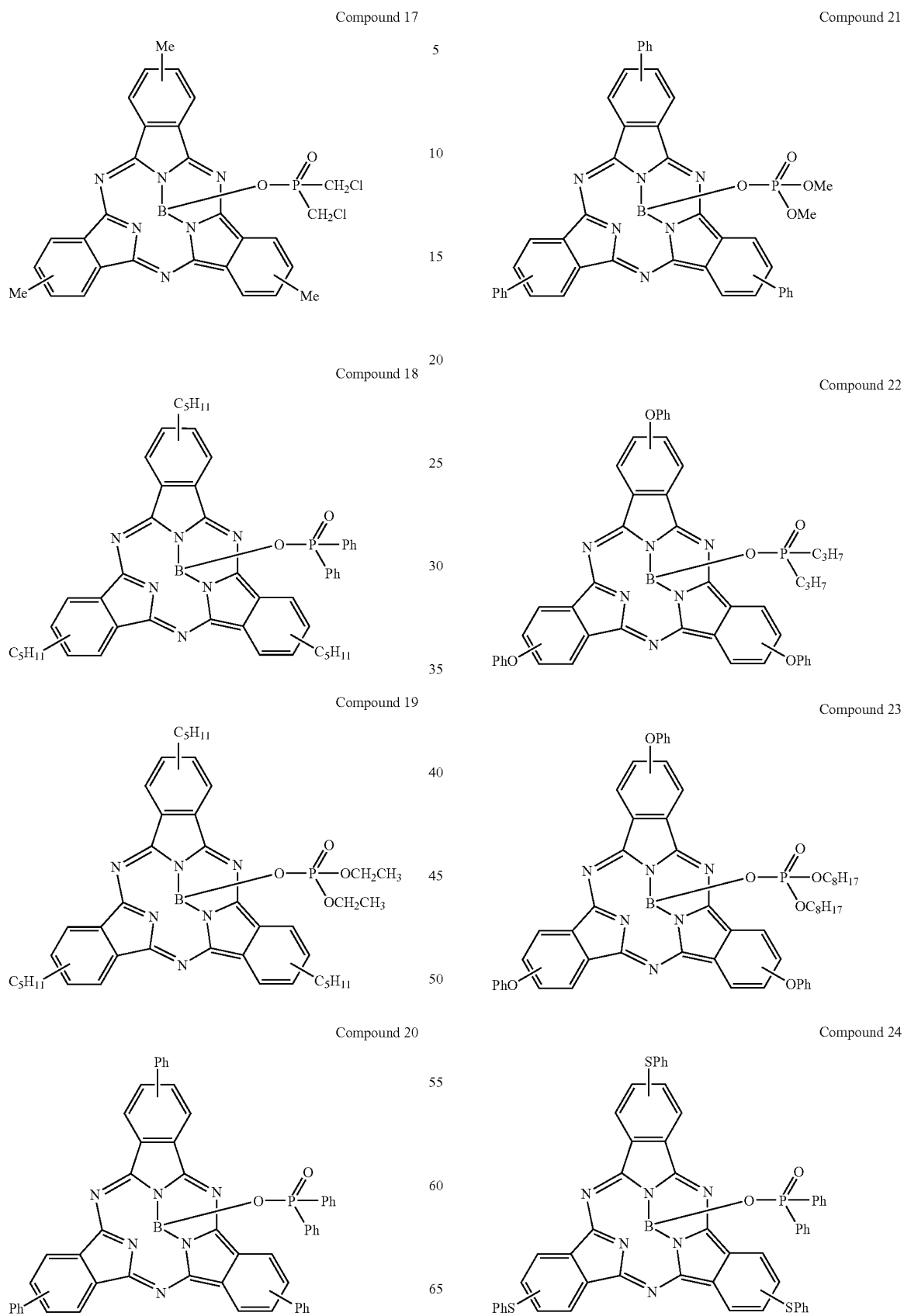

Compound 25
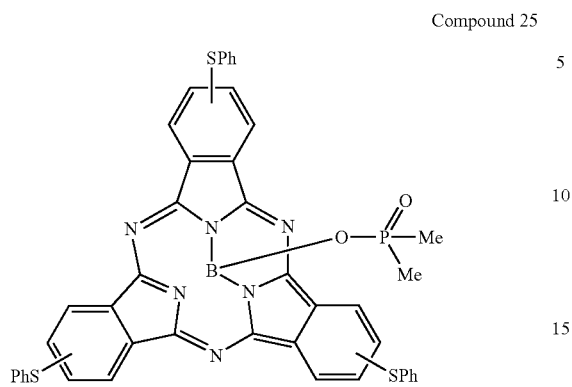
Compound 26
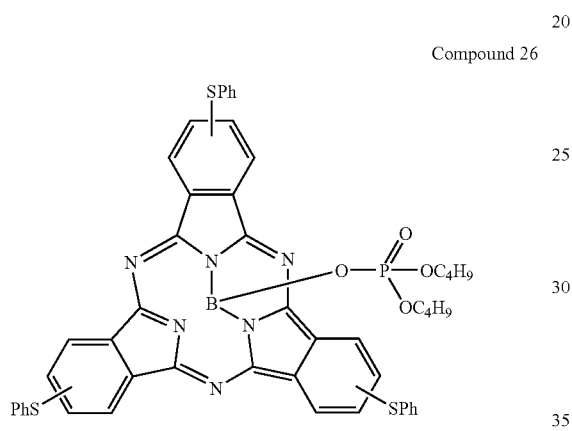
Compound 27
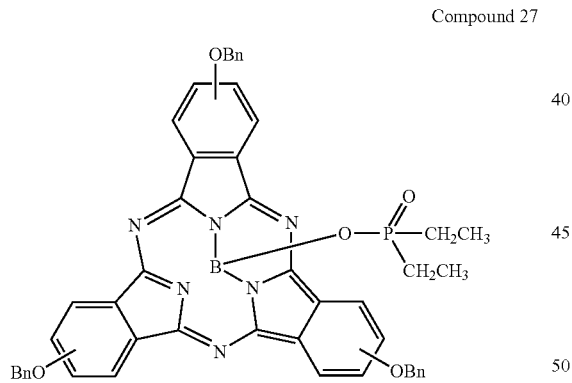
Compound 28
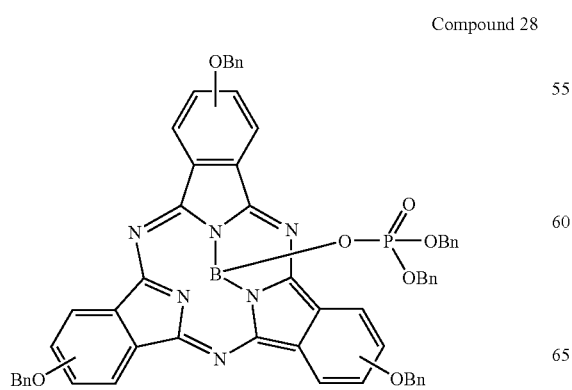
Compound 29
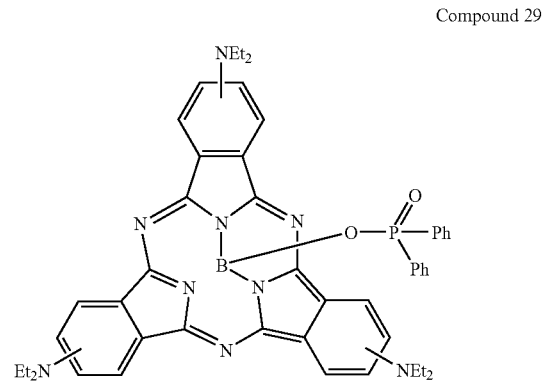
Compound 30
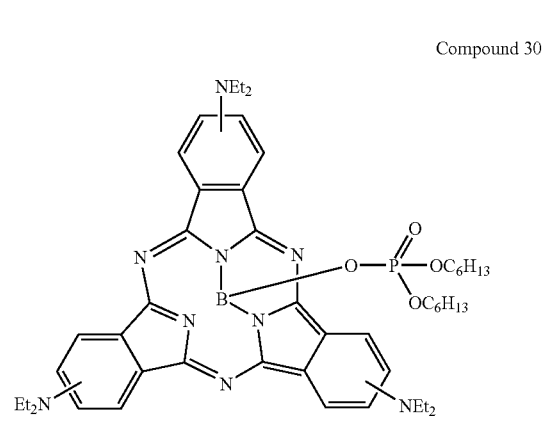
Compound 31
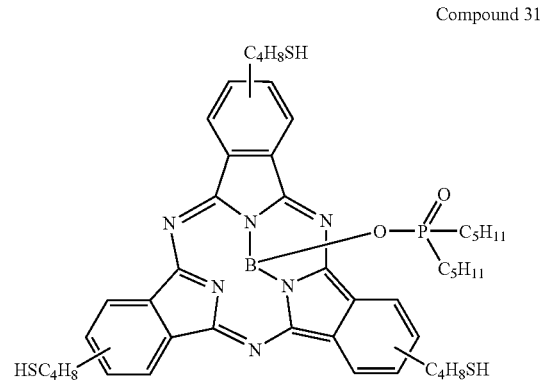
Compound 32
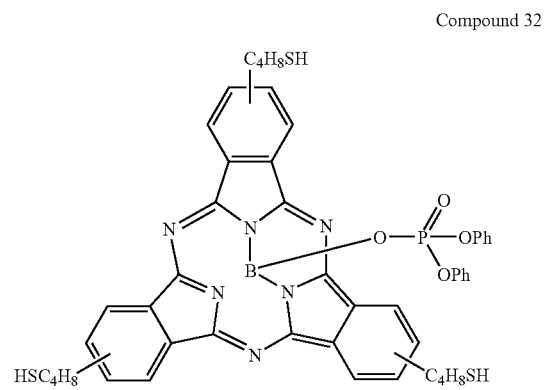

Compound 33
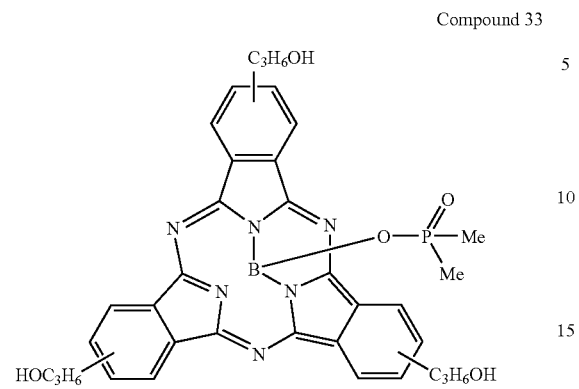
Compound 34
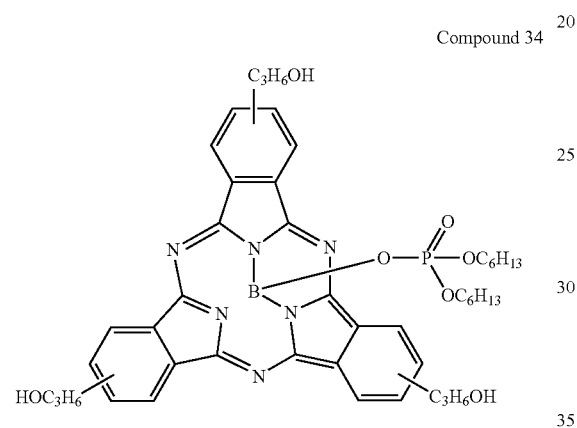
Compound 35
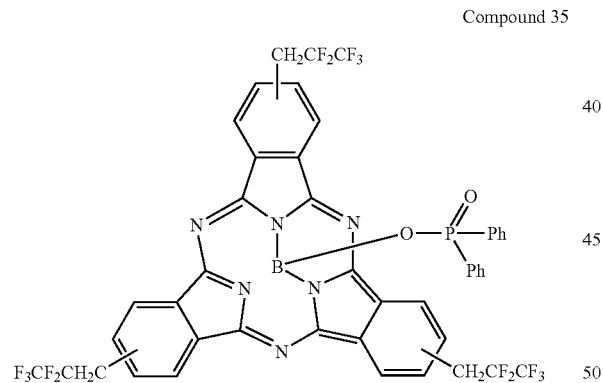
Compound 36
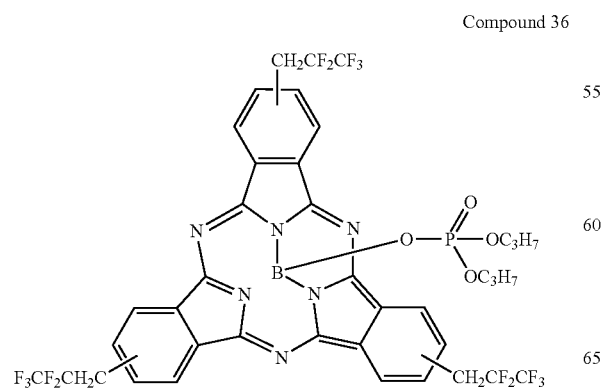
Compound 37
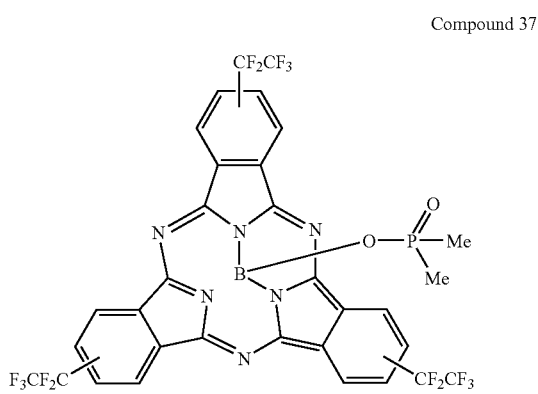
Compound 38
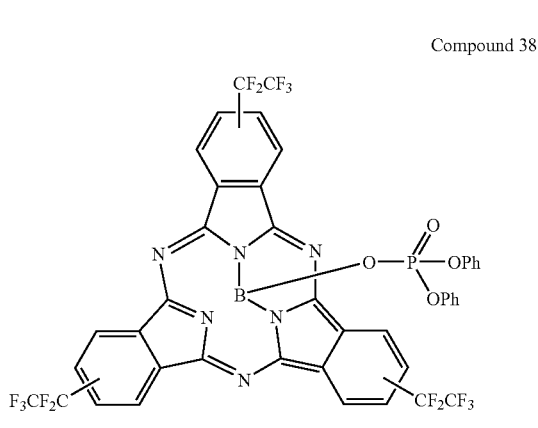
Compound 39
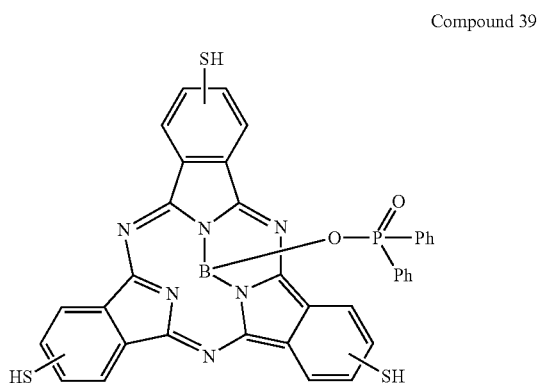
Compound 40
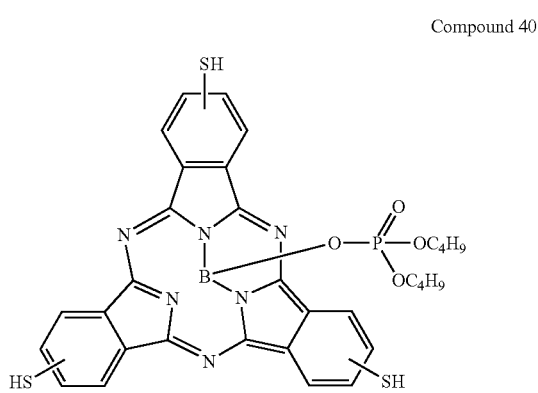

Compound 41

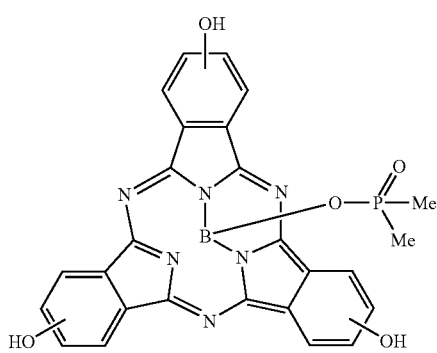

Compound 42

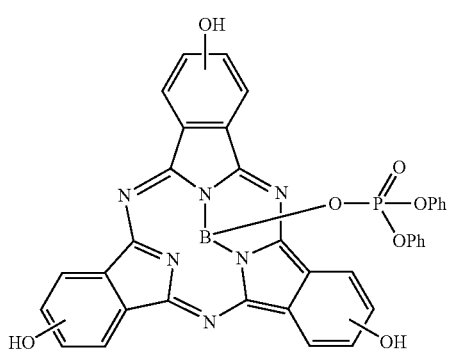

Compound 43

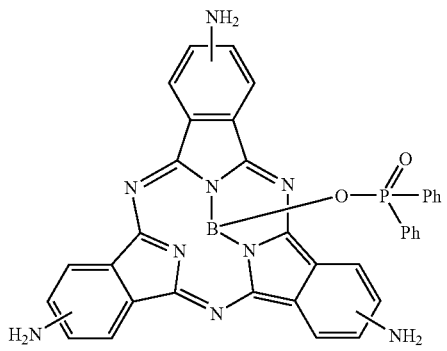

Compound 44

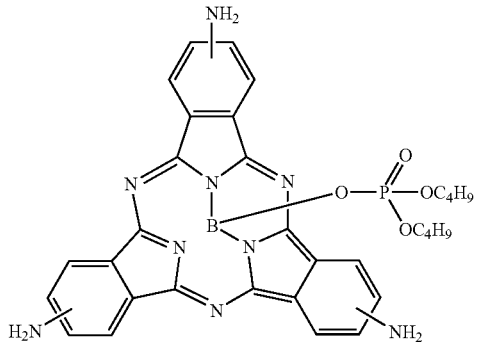

Next, the present optical film which is a functional optical thin film containing the subphthalocyanine derivative having the phosphorus derivative-substituted group is explained.

This optical film is the functional optical thin film such as a light-transmissive thin film. The light-transmissive thin film including it as the coloring matter has functions that the thin film absorbs or blocks light in a specific wavelength and can take out desired wavelength light.

The light-transmissive thin film is characterized by containing the subphthalocyanine derivative having the phosphorus derivative-substituted group therein. The subphthalocyanine derivative having the phosphorus derivative-substituted group has a narrow half width and suppresses broadening of a light wavelength due to molecular association of the coloring matter in the thin film. Therefore, by appropriately selecting the derivatives of the present invention, light having a specific and narrow wavelength in 510-610 nm which causes images on display devices to become blurry, can be selectively blocked by the light-transmissive thin film.

The light having a wavelength at around 560 nm is equivalent to that of green light and corresponds to the light at the middle of the human visual sensitivity Therefore, human tends to visually recognize this light strongly. And the orange light having wavelength of 520-620 nm, particularly at around 580 nm is one of the causes which degrades the sharpness of the images.

This light-transmissive thin film containing the coloring matter whose main component is the subphthalocyanine derivative having the phosphorus derivative-substituted group represented by the formula (1) improves the contrast of the display and accordingly clear images can be obtained. This coloring matter has a property of absorbing light in 530-590 nm wavelength, so this film can be preferably used as a light-transmissive thin film and a functional optical thin film such as an antireflection thin film.

For instance, the optical film can be manufactured by applying an optical-film coating material such as an optical-film ink on a substrate. The coating material contains coloring matter whose main component is the subphthalocyanine derivative having the phosphorus derivative-substituted group in which the phosphorus derivative-substituted group as the axially substituted group is connected to the boron atom thereof.

The light-transmissive thin film is formed by applying the coating material such as ink on the substrate to adhere the coloring matter thereon. In the coating material, the subphthalocyanine derivative having the phosphorus derivative-substituted group is mainly dissolved as the coloring matter. The amount of the subphthalocyanine derivative having the phosphorus derivative-substituted group in the coating material is preferably 0.0001-10% by weight, more preferably 0.001-5% by weight, still more preferably 0.005-3% by weight based on the total amount of the coating material.

The molar absorbance coefficient of the coloring matter used for the light-transmissive thin film is preferably 55,000-150,000 $Lmol^{-1} cm^{-1}$, more preferably 60,000-100,000 $Lmol^{-1} cm^{-1}$.

Next, another optical film of the present invention is explained. The optical film can be a functional optical thin film used such as for an antireflection thin film. The antireflection thin film is used for improving visibility by preventing the reflection of a fluorescent bulb or backgrounds in the surface of the display screen.

The antireflection thin film is characterized by containing the subphthalocyanine derivative having the phosphorus derivative-substituted group as a light absorber. The present subphthalocyanine derivative having the phosphorus derivative-substituted group absorbs light in the wavelength of 510-610 nm, light at around 560 nm which corresponds to the center wavelength of the human visual sensitivity and orange light (550-620 nm), all of which deteriorates the sharpness of images. Accordingly, clear images can be obtained. Furthermore, the present subphthalocyanine derivative having the phosphorus derivative-substituted group has a small half width so that it does not deteriorate the color purity of the neighboring red light, being also able to display clear images.

In the functional optical thin film such as the light-transmissive thin film or the antireflection thin film, other functional materials can be added in a range without deteriorating the optical properties of the present subphthalocyanine derivative having the phosphorus derivative-substituted group. As other functional materials, a near-infrared absorbent, an ultraviolet absorbing absorbent, an adjusting agent for color tone etc., which may be colorant, can be exemplified.

The near-infrared absorbents are used to prevent a false operation of a home electric appliance, speaker noise due to interference at the receiving part of a microphone, false operation of an automatic door etc. caused by near infrared ray. Preferably the near-infrared absorbents transmit light in visible wavelength region and preferably absorb only near-infrared ray region (900-1,200 nm). Many substances of the near-infrared absorbents are organic colorant.

As such organic colorant, a dithiol metal complex, a cyanine type compound, a diimmonium type compound, a phthalocyanine type compound, a naphthalocyanine type compound etc. can be exemplified. The organic colorant can be used alone or in combination of two or more. In addition, the manner and methods of adding such organic colorant are not specifically limited. The coloring matter can be added into the coating material such as an ink which is used for a functional optical film. And various film-forming methods such as a calendaring method, a coating method, a casting method etc. can be adopted.

As the ultraviolet absorbent, both inorganic and organic series can be used but organic ultraviolet absorbent can be practically used. An organic ultraviolet absorbent that absorbs light in the range of 300-400 nm, preferably has the largest absorption wavelength peak at around 350 nm and has a light absorption rate of 80% or more is preferably used. For example, a compound of a benzotriazole type, a benzophenone type, a salicylic acid ester type, an acrylate type, an oxalic acid anilide type, a hindered amine type etc. can be exemplified. Such ultraviolet absorbents can be used alone or in combination of two or more. Preferably, several kinds of them are used in combination. The method of adding these ultraviolet absorbents are not specifically limited but may be added into a coating material, for example a optical functional ink. Film forming of them can be carried out by a calendaring method, a coating method, a casting method etc.

The adjusting agents for the color tone are used for correcting color balance of displayed colors and improving contrast of display images. As the adjusting agents for the color tone, for example, colorant of a cyanine (polymethine) type, a quinine type, an azo type, an indigo type, a polyene type, a spiro type, a porphyrin type, a phthalocyanine type, a naphthalocyanine type etc. can be exemplified. Such colorant can be used alone or in combination of two or more. Preferably several kinds of such colorant are used in combination.

As a method to produce the optical films such as the functional optical thin films, an ink jet recording method, a physical vapor deposition (PVD) method, a chemical vapor deposition (CVD) method, a calendering method, a coating method, a casting method, a dipping method, etc. can be exemplified. Among the PVD methods, a vacuum deposition method can be specifically used. In the vacuum deposition method, organic colorant or metal oxide is heated in vacuum and deposited on a substrate (for example between two electrode layers), thus forming a thin film.

The subphthalocyanine derivatives having the phosphorus derivative-substituted group can be formed into a thin film using the vacuum deposition method.

Coating materials containing the subphthalocyanine derivative having the phosphorus derivative-substituted group can be formed into thin films using spin coating method etc. The subphthalocyanine derivatives having the phosphorus derivative-substituted group have high solubility to various solvents and also have excellent resistance to light and heat so that the resulting film is excellent in toughness.

Further, the subphthalocyanine derivatives having the phosphorus derivative-substituted group can be used as dyes and have excellent light resistance and heat resistance. Therefore, these coating materials can be preferably used as inks for forming light absorbing layers of displays of displaying devices. When light absorbing layers are formed on substrates or for examples on the displays of the displaying devices, the substrates or displaying devices can be provided with antireflection function or light blocking function to block out unnecessary light.

As a medium of the coating material, a ketone series solvent such as acetone, methyl ethyl ketone, cyclohexanone, 4-methoxy-4-methyl pentanone etc.; a hydrocarbon series solvent such as cyclohexane, methylcyclohexane, n-pentane, n-hexane, n-heptane etc.; an alcohol series solvent such as methanol, ethanol, propanol, isopropanol etc.; a glycol and its ether series solvent such as a polyol represented by ethylene glycol, diethylene glycol, propylene glycol, glycerine, dipropylene glycol, 1, 2-hexanediol, 2,4,6-hexanetriol etc., dioxane, methyl cellosolve, ethyl cellosolve, butyl cellosolve, diethylene glycol mono-butyl ether, ethylene glycol mono-butyl ether, ethylene glycol mono-ethyl ether etc.; an ester series solvent such as ethyl acetate, butyl acetate, n-propyl acetate etc.; a halogenated solvent such as 1,2-dichloroethane, dichloromethane, 1,1,2-trichloroethane, chloroform etc.; an aromatic series solvent such as toluene, xylene etc.; dimethyl sulfoxide, N-methyl-2-pyrrolidone, 2-pyrrolidone; •-butyrolactone: tetrahydrofuran(THF) etc.; can be exemplified. These mediums can be used alone or in combination of two or more. These mediums can be used with a little water.

Among them, a ketone series solvent such as acetone, methyl ethyl ketone, cyclohexanone; an alcohol series solvent such as methanol, ethanol, isopropanol; an aromatic series solvent such as toluene, xylene; an ester series solvent such as an ethyl acetate, butyl acetate, n-propyl acetate; N-methyl-2-pyrrolidone; dimethyl sulfoxide; ethylene glycol; are preferable.

The coating material may further contain various additives as ingredients. As the additive, a binder (resin), a penetrant, an antifoaming agent, a colorant, an antioxidant, a UV absorbent, a lubricant, an antiseptic, a fungicide, an anticorrosive, a dispersant, a rheology control agent, a surfactant, a PH adjuster, a film modifier, a charge control agent, an animal and a plant oil etc. can be exemplified. These additives may be optionally selected and used alone or in combination of two or more.

The binder (resin) ingredient is used to firmly fix the subphthalocyanine derivative having the phosphorus derivative-substituted group in place, to stabilize the ink and to adjust the viscosity of the ink. Any publicly known resins can be used as long as the resins are soluble in the aforementioned mediums.

As the binder ingredient, a polyvinyl series resin such as a polyvinylalcohol, a polyvinylbutyral, a polyvinylpyrrolidone, a vinylpyrrolidone-vinyl acetate copolymer etc.; a polyamine series resin such as a polyallylamine, a polyvinylamine, a polyethylenimine etc. a polyacrylate series resin such as a polymethylacrylate, a polyethylene-acrylate copolymer, a polymethylmethacrylate, a polyvinylmethacrylate, etc.; a rosin, a rosin modified resin (phenol, maleic acid or fumaric acid resins); a cellulose series resins such as a ethylcellulose, a nitrocellulose etc.; a polyolefin resins such as a polyethylene resin, a polypropylene resin etc.; a phenol modified xylene resin; a xylene resin; a terpene-phenol resin; a phenol resin; a ketone resin; an acryl resin; a stylene-acryl resin; a styrene-maleic acid resin; a polyterpene resin; a polyterpene-maleic acid resin; a polystyrene resin; a polyurethane resin; an acrylic urethane resin; a polyester resin; a vinyl chloride resin; a vinylidene chloride resin; a polyvinyl formal resin and its copolymer; an alkyd resin; an epoxy resin; a polyester imide resin; a polyamide resin; polyamideimide resin; a silicone resin; a fluoro resin (fluoropolymer); a natural resin (gum arabic, gelatin etc.) etc. can be exemplified. These resins can be used alone or in combination of two or more.

The coating material can be prepared by mixing the subphthalocyanine derivative having the phosphorus derivative-substituted group, medium, and if necessary the binder and the additives, and stirring the mixture to dissolve them, if necessary diluting them and adding another additives. Mixing and stirring can be carried out using an ordinary rotor blade, high speed mill or emulsifying machine etc.

The resulting coating material is, if necessary filtered and purified before or after dilution. The filtration is carried out using a filter having a pore diameter of not more than 3.0 •m, preferably 1.0 •m.

This coating material is used as ink for forming the functional optical thin film such as the light-transmissive thin film and the antireflection film.

The present invention will be explained more precisely by referring to the following Examples of the present optical films.

Hereinafter, it is noted that the symbol of "SubPcB" in this specification represents the "boron subphthalocyanine".

Synthesis of Halo Boron Subphthalocyanine

The halo boron subphthalocyanine was synthesized according to the procedure described in Japanese Patent Publication No. 2005-289854A and Japanese Patent Application No. 2007-053265. The synthesis procedure of the halo boron subphthalocyanine will be precisely explained by referring to concrete examples.

Synthesis Example 1

Synthesis of Intermediate Compound 1

A mixture of 76.8 g of phthalonitrile, 260 g of p-xylene and 270 g of 1.0 M of boron trichloride/p-xylene solution was stirred over a period of 1 hour under a nitogen gas stream at a reflux temperature. 29.3 g of SubPcBCl (Intermediate Compound 1) was obtained.

Synthesis Example 2

Synthesis of Intermediate Compound 2

A mixture of 25.0 g of 4-t-butyl phthalonitrile, 58.9 g of p-xylene and 61.3 g of 1.0M boron trichloride/p-xylene solution was stirred over a period of 2 hours under a nitrogen gas stream at a reflux temperature. 12.7 g of $(t-Bu)_3$ SubPcBCl (Intermediate Compound 2) was obtained.

Synthesis Example 3

Synthesis of Intermediate Compound 6

A mixture of 140 g of i-pentylthio phthalonitrile, 353 g of p-xylene and 337 g of 1.0M boron trichloride/p-xylene solution was stirred over a period of 2 hours under a nitrogen gas stream at a reflux temperature. 65.5 g of $(i-C_5H_{11}S)_3$ SubPcBCl (Intermediate Compound 6) was obtained.

Synthesis Example 4

Synthesis of Intermediate Compound 11

A mixture of 35.0 g of phenylthio phthalonitrile, 86 g of p-xylene and 82 g of 1.0M boron trichloride/p-xylene solution was stirred over a period of 2 hours under a nitrogen gas stream at a reflux temperature. 18.2 g of $(PhS)_3SubPcBCl$ (Intermediate Compound 11) was obtained.

The procedure of the synthesis of the subphthalocyanine derivative having the phosphorus derivative-substituted group is precisely explained by referring to concrete examples.

Example 1

Synthesis of Compound 1

1.0 g of Intermediate Compound 1 obtained in Synthesis Example 1 and 11.0 g of diphenylphosphinic acid were added into volume of 40 ml of orthodichlorobenzene. The reaction mixture was stirred at reflux over a period of 6 hours. After the reaction, the reaction mixture was filtered and concentrated, and then purified using silica gel column chromatography (developing solvent: ethyl acetate:chloroform=1:1), 1.0 g of $SubPcBOPOPh_2$ (Compound 1) was obtained (yield: 67.4%, starting from the Intermediate Compound 1).

Results of the elemental analysis of $SubPcBOPOPh_2$ (Compound 1) are shown in Table 1. Molecular formula of the Compound 1 is $C_{36}H_{22}N_6BO_2P$.

TABLE 1

| | C | H | N |
|---|---|---|---|
| Value (%) calculated | 70.61 | 3.62 | 13.72 |
| Value (%) observed | 69.07 | 3.47 | 13.04 |

Yield, maximum absorption wavelength and molar absorbance coefficient in chloroform are shown in Table 10. And observed solubility is shown in Table 11. From the observed results it was confirmed that $SubPcBOPPh_2$ (Compound 1) had the aforementioned chemical formula.

Results of $^1$H-NMR measurement of Compound 1 are shown below.

NMR (300 MHz)

$^1$H-NMR (CDCl$_3$): • 6.84 (m, 4H), 6.97 (m, 4H), 7.08 (m, 2H), 7.77 (m, 6H), 8.71 (m, 6H) ppm $^{13}$C-NMR (CDCl$_3$): • 122.2, 127.6, 127.8, 129.7, 130.3, 130.5, 130.9, 130.9, 131.0, 131.6, 133.5, 150.6 ppm IR (KBr): • 1731, 1456, 1434 (P-Ph), 1226, 1132, 1041 (P—O), 734, 698, 532 cm$^{-1}$ Example 2

Synthesis of Compound 3

1.0 g of Intermediate Compound 1 obtained in Synthesis Example 1 and 1.2 g of diphenyl phosphate were added into volume of 40 ml of orthodichlorobenzene. The reaction mixture was stirred at reflux over a period of 5 hours. After the reaction, the reaction mixture was filtered and concentrated, and then purified using silica gel column chromatography (developing solvent: toluene). 1.0 g of SubPcBOPO(OPh)$_2$ (Compound 3) (yield: 64.4%, starting from Intermediate Compound 1).

Results of the elemental analysis of SubPcBOPO(OPh)$_2$ (Compound 3) is shown in Table 2. Molecular formula of Compound 3 is $C_{36}H_{22}N_6BO_4P$.

TABLE 2

|  | C | H | N |
|---|---|---|---|
| Value (%) calculated | 76.10 | 3.44 | 13.04 |
| Value (%) observed | 64.64 | 3.31 | 12.34 |

Yield, maximum absorption wavelength and molar absorbance coefficient in chloroform are shown in Table 10. And observed solubility is shown in Table 11. From the observed results it was confirmed that SubPcBOPO(OPh)$_2$ (Compound 3) had the structure of the aforementioned chemical formula.

Results of $^1$H-NMR measurement of Compound 3 are shown below.

NMR (300 MHz)
$^1$H-NMR (CDCl$_3$): • 6.56 (d, J=8.7 Hz, 4H), 6.93 (t, J=6.6 Hz, 2H), 7.03 (t, J=8.4 Hz, 4H), 7.90 (m, 6H), 8.83 (m, 6H) ppm
$^{13}$C-NMR (CDCl$_3$): • 119.5, 119.5, 122.3, 123.6, 123.5, 129.3, 130.0, 131.0, 134.3, 149.9, 150.0, 150.9 ppm
IR (KBr): • 1727, 1589, 1456, 1288 (P—OPh), 1051, 1024 (P—O), 944, 740, 509 cm$^{-1}$ Example 3

Synthesis of Compound 4

1.0 g of Intermediate Compound 1 obtained in Synthesis Example 1 and 1.0 g of dibutyl phosphate were added into volume of 40 ml of orthodichlorobenzene. The reaction mixture was stirred at reflux over a period of 11 hours. After the reaction, the reaction mixture was filtered and concentrated, and then purified using silica gel column chromatography (developing solvent: ethyl acetate:toluene=1:1). 0.5 g of SubPcBOPO(OBu)$_2$ (Compound 4) was obtained (yield: 34.3%, starting from Intermediate Compound 1).

Results of the elemental analysis of SubPcBOPO(OBu)$_2$ (Compound 4) are shown in Table 3. Molecular formula of Compound 4 is $C_{32}H_{30}N_6BO_4P$.

TABLE 3

|  | C | H | N |
|---|---|---|---|
| Value (%) calculated | 63.59 | 5.00 | 13.90 |
| Value (%) observed | 63.39 | 4.70 | 13.75 |

Yield, maximum absorption wavelength and molar absorbance coefficient in chloroform are shown in Table 10. And observed solubility is shown in Table 11. From the observed results, it was confirmed that SubPcBOPO (OBu)$_2$ (Compound 4) had the structure of the aforementioned chemical formula.

Results of $^1$H-NMR measurement of Compound 4 are shown below.

NMR (300 MHz)
$^1$H-NMR (CDCl$_3$): • 0.70 (t, J=7.2 Hz, 6H), 1.02 (m, 4H), 1.17 (m, 4H), 3.20 (q, J=6.9 Hz, 4H), 7.91 (m, 6H), 8.86 (m, 6H) ppm
$^{13}$C-NMR (CDCl$_3$): • 13.5, 18.5, 31.9, 32.0, 66.1, 66.2, 122.3, 129.9, 131.0, 150.8 ppm
IR (KBr): • 1456, 1286, 1133, 1052 (P—OBu), 1025 (P—O), 738, 511 cm$^{-1}$ Example 4

Synthesis of Compound 5

2.0 g of Intermediate Compound 2 obtained in Synthesis Example 2 and 1.5 g of diphenylphosphinic acid were added into volume of 40 ml of orthodichlorobenzene. The reaction mixture was stirred at reflux over a period of 5 hours. After the reaction, the reaction mixture was filtered and concentrated, and then purified using silica gel column chromatography (developing solvent: toluene: ethyl acetate=5:1).
0.6 g (t-Bu)$_3$SubPcBOPOPh$_2$ (Compound 5) was obtained (yield: 23.3%, starting from Intermediate Compound 5).

Results of the elemental analysis of (t-Bu)$_3$SubPcBOPOPh$_2$ (Compound 5) are shown in Table 4. Molecular formula of Compound 5 is $C_{48}H_{46}N_6BO_2P$.

TABLE 4

|  | C | H | N |
|---|---|---|---|
| Value (%) calculated | 73.85 | 5.94 | 10.76 |
| Value (%) observed | 71.77 | 5.60 | 8.73 |

Yield, maximum absorption wavelength and molar absorbance coefficient in chloroform are shown in Table 10. And observed solubility is shown in Table 11. From the observed results, it was confirmed that (t-Bu)$_3$SubPcBOPOPh$_2$ (Compound 5) had the structure of the aforementioned chemical formula.

Results of $^1$H-NMR measurement of Compound 5 are shown below.

NMR (300 MHz)
$^1$H-NMR (CDCl$_3$): • 1.47 (s, 18H), 6.81 (m, 4H), 6.95 (m, 4H), 7.05 (m, 2H), 7.88 (m, 2H), 8.65 (m, 2H), 8.76 (m, 2H) ppm
$^{13}$C-NMR (CDCl$_3$): • 31.3, 31.6, 35.8, 118.4, 121.7, 125.2, 127.7, 127.8, 130.4, 130.8, 150.3, 153.8 ppm
IR (KBr): • 2960, 1573, 1436 (P-Ph), 1035 (P—O), 1022, 696, 528 cm$^{-1}$ Example 5

Synthesis of Compound 7

2.0 g of Intermediate Compound 2 obtained in Synthesis Example 2 and 1.4 g of dibutyl phosphate were added into volume of 80 ml of orthodichlorobenzene. The reaction mixture was stirred at reflux over a period of 5 hours. After the reaction, the reaction mixture was filtered and concentrated and then purified using silica gel column chromatography (developing solvent: toluene:ethyl acetate=5:1). 0.5 g of (t-Bu)$_3$SubPcBOPO(OBu)$_2$ (Compound 7) was obtained (yield: 18.8%, starting from Intermediate Compound 2).

Results of the elemental analysis of (t-Bu)$_3$SubPcBOPO(OBu)$_2$ (Compound 7) are shown in Table 5. Molecular formula of Compound 7 is C$_{44}$H$_{54}$N$_6$BO$_4$P.

TABLE 5

|  | C | H | N |
| --- | --- | --- | --- |
| Value (%) calculated | 68.39 | 7.04 | 10.88 |
| Value (%) observed | 67.84 | 7.35 | 10.57 |

Yield, maximum absorption wavelength and molar absorbance coefficient in chloroform are shown in Table 10. And observed solubility is shown in Table 11. From the observed results, it was confirmed that (t-Bu)$_3$SubPcBOPO(OBu)$_2$ (Compound 7) had the structure of aforementioned chemical formula.

Results of $^1$H-NMR measurement of Compound 7 are shown below.

NMR (300 MHz)
$^1$H-NMR (CDCl$_3$): • 0.70 (t, J=7.5 Hz, 6H), 1.00 (m, 4H), 1.15 (m, 4H), 1.53 (s, 18H), 3.18 (q, J=6.6 Hz, 4H), 7.97 (d, J=7.8 Hz, 2H), 8.77 (t, J=8, 1 Hz, 2H), 8.87 (d, J=7.5 Hz, 2H) ppm
$^{13}$C-NMR (CDCl$_3$): • 13.5, 18.4, 31.5, 31.9, 35.7, 66.0, 118.3, 121.7, 127.9, 128.6, 131.2, 150.7, 153.8 ppm
IR (KBr): • 2958, 1278, 1182, 1054 (P—OBu), 1025 (P-0), 711, 541 cm$^{-1}$ Example 6

Synthesis of Compound 11

1.0 g of Intermediate Compound 6 obtained in Synthesis Example 3 and 0.6 g of diphenylphosphinic acid were added into volume of 40 ml of orthodichlorobenzene. The reaction mixture was stirred at reflux over a period of 6 hours. After the reaction, the reaction mixture was flittered and concentrated and then purified using silica gel column chromatography (developing solvent: hexane:ethyl acetate=3:1). 0.7 g of (i-C$_5$H$_{11}$S)$_3$SubPcBOPOPh$_2$ (Compound 11) was obtained (yield: 57.6%, starting from Intermediate Compound).

Results of the elemental analysis of (i-C$_5$H$_{11}$S)$_3$SubPcBOPOPh$_2$ (Compound 11) are shown in Table 6. Molecular formula of Compound 11 is C$_{51}$H$_{52}$N$_6$BO$_2$PS$_3$.

TABLE 6

|  | C | H | N | S |
| --- | --- | --- | --- | --- |
| Value (%) calculated | 66.65 | 5.70 | 9.14 | 10.47 |
| Value (%) observed | 63.20 | 5.47 | 8.22 | 10.00 |

Yield, maximum absorption wavelength and molar absorbance coefficient in chloroform are shown in Table 10. And observed solubility is shown in Table 11. From the observed results, it was confirmed that (i-C$_5$H$_{11}$S)$_3$SubPcBOPOPh$_2$ (Compound 11) had the structure of aforementioned chemical formula.

Results of $^1$H-NMR measurement of Compound 11 are shown below.

NMR (300 MHz)
$^1$H-NMR (CDCl$_3$): • 1.00 (d, J=6.9 Hz, 18H), 1.68 (q, J=7.5 Hz, 6H), 1.84 (m, 3H), 3.20 (m, 6H), 6.92 (m, 4H), 7.07 (m, 4H), 7.18 (m, 2H), 7.75 (d, J=8.4 Hz, 3H), 8.62 (s, 3H), 8.63 (d, J=4.8 Hz, 6H) ppm
$^{13}$C-NMR (CDCl$_3$): • 21.2, 22.3, 27.5, 31.1, 37.5, 119.8, 122.1, 127.6, 129.2, 130.3, 130.5, 131.0, 141.1, 141.2, 149.3, 149.8, 150.0, 150.4, 151.1 ppm
IR (KBr): • 2954, 1606, 1436 (P-Ph), 1037 (P—O), 1024, 698, 532 cm$^{-1}$ Example 7

Synthesis of Compound 13

2.0 g of Intermediate Compound 6 obtained in Synthesis Example 3 and 1.4 g of diphenyl phosphate were added into volume of 80 ml of orthodichlorobenzene. The reaction mixture was stirred at reflux over a period of 6 hours. After the reaction, the reaction mixture was filtered and concentrated and then purified using silica gel chromatography (developing solvent: toluene:ethyl acetate=3:1). 1.2 g of (i-C$_5$H$_{11}$S)$_3$SubPcBOPO(OPh)$_2$ (Compound 13) was obtained (yield: 46.9%, starting from Intermediate Compound 6).

Results of the elemental analysis of (i-C$_5$H$_{11}$S)$_3$SubPcBOPO(OPh)$_2$ (Compound 13) are shown in Table 7. Molecular formula of Compound 13 was C$_{51}$H$_{52}$N$_6$BO$_4$PS$_3$.

TABLE 7

|  | C | H | N | S |
| --- | --- | --- | --- | --- |
| Value (%) Calculated | 64.41 | 5.51 | 8.84 | 10.12 |
| Value (%) observed | 63.53 | 5.36 | 8.44 | 10.10 |

Yield, maximum absorption wavelength and molar absorbance coefficient in chloroform are shown in Table 10. And observed solubility is shown in Table 11. From the observed results, it was confirmed that (i-C$_5$H$_{11}$S)$_3$SubPcBOPO(OPh)$_2$ (Compound 13) had the structure of aforementioned chemical formula.

Results of $^1$H-NMR measurements of Compound 13 are shown below.

NMR (300 MHz)
$^1$H-NMR (CDCl$_3$): • 1.00 (d, J=6.9 Hz, 18H), 1.66 (q, J=7.5 Hz, 6H), 1.83 (m, 3H), 3.20 (m, 6H), 6.56 (d, J=7, 2 Hz, 4H), 6.94 (t, J=6.9 Hz, 2H), 7.05 (t, J=7.8 Hz, 4H), 7.75 (d, J=8.4 Hz, 3H), 8.63 (s, 3H), 8.65 (d, J=4.8 Hz, 6H) ppm
$^{13}$C-NMR (CDCl$_3$): • 21.2, 22.3, 27.5, 31.1, 37.5, 119.5, 119.8, 122.2, 124.5, 127.8, 129.3, 131.8, 141.5, 141.6, 149.3, 149.8, 150.0, 150.4, 151.1 ppm
IR (KBr): • 2954, 1604, 1440, 1294 (P—OPh), 1191, 1047, 1024 (P—O), 943, 755, 584 cm$^{-1}$ Example 8

Synthesis of Compound 24

2.0 g of Intermediate Compound 11 obtained in Synthesis Example 4 and 1.2 g of diphenylphosphinic acid were added into volume of 80 ml of orthodichlorobenzene. The reaction mixture was stirred at reflux over a period of 8 hours. After the reaction, the reaction mixture was filtered and concentrated and then purified using silica gel column chromatography (developing solvent: hexane:ethyl acetate=2:1). 1.4 g of (PhS)$_3$SubPcBOPOPh$_2$ (Compound 24) was obtained (yield: 56.0%, starting from Intermediate Compound 11).

Results of the elemental analysis of (PhS)$_3$SubPcBOPOPh$_2$ (Compound 24) are shown in Table 8. Molecular formula of Compound 24 is C$_{54}$H$_{34}$N$_6$BO$_2$PS$_3$.

TABLE 8

|  | C | H | N | S |
|---|---|---|---|---|
| Value (%) calculated | 69.23 | 3.66 | 8.97 | 10.27 |
| Value (%) observed | 66.99 | 3.49 | 8.29 | 9.41 |

Yield, maximum absorption wavelength and molar absorbance coefficient in chloroform are shown in Table 10. And observed solubility is shown in Table 11. From the observed results, it was confirmed that $(PhS)_3SubPcBOPOPh_2$ (Compound 24) had the structure of aforementioned chemical formula.

Results of $^1$H-NMR measurement of Compound 24 are shown below.

NMR (300 MHz)
$^1$H-NMR (CDCl$_3$): • 6.87 (m, 4H), 7.02 (m, 4H), 7.15 (m, 2H), 7.38 (m, 9H), 7.48 (m, 6H), 7.71 (m, 3H), 8.58 (m, 6H) ppm
$^{13}$C-NMR (CDCl$_3$): • 122.6, 122.8, 127.7, 127.9, 128.2, 129.6, 130.3, 130.5, 130.9, 131.1, 132.5, 132.6, 140.4, 140.5, 150.3, 150.5, 150.8 ppm
IR (KBr): • 1606, 1436 (P-Ph), 1037 (P—O), 1024, 748, 690, 532 cm$^{-1}$ Example 9

Synthesis of Compound 26

2.0 g of Intermediate Composition 11 obtained in Synthesis Example 4 and 1.1 g of dibutyl phosphate were added into volume of 80 ml of orthodichlorobenzene. The reaction mixture was stirred at reflux over a period of 6 hours. After the reaction, the reaction mixture was filtered and concentrated and then purified using silica gel column chromatography (developing solvent: toluene: ethylacetate=1:1). 1.0 g of $(PhS)_3SubPcBOPO(OBu)_2$ (Compound 26) was obtained (yield: 40.0%, starting from Intermediate Compound 11).

Results of the elemental analysis of $(PhS)_3SubPcBOPO(OBu)_2$ (Compound 26) are shown in Table 9. Molecular formula of Compound 26 is $C_{50}H_{42}N_6BO_4PS_3$.

TABLE 9

|  | C | H | N | S |
|---|---|---|---|---|
| Value (%) calculated | 64.65 | 4.56 | 9.05 | 10.36 |
| Value (%) observed | 64.00 | 4.39 | 8.63 | 9.94 |

Yield, maximum absorption wavelength in chloroform and molar absorbance coefficient are shown in Table 10. And observed solubility is shown in Table 11. From the measured results, it was confirmed that $(PhS)_3SubPcBOPO(OBu)_2$ (Compound 26) had the structure of the aforementioned chemical formula.

Results of $^1$H-NMR measurement of Compound 26 are shown below.

NMR (300 MHz)
$^1$H-NMR (CDCl$_3$): • 0.71 (t, J=7.5 Hz, 6H), 1.00 (m, 4H), 1.16 (m, 4H), 3.18 (q, J=6.6 Hz, 4H), 7.38 (m, 9H), 7.50 (m, 6H), 7.73 (m, 3H), 8.67 (m, 6H) ppm
$^{13}$C-NMR (CDCl$_3$): • 13.5, 18.5, 31.9, 66.2, 122.6, 122.7, 129.7, 130.8, 130.9, 132.7, 132.8, 133.8, 140.7, 140.9, 150.2, 150.3, 150.6 ppm
IR (KBr): • 1606, 1438, 1184, 1052 (P—OBu), 1024 (P—O), 750, 705, 526 cm$^{-1}$ Measuring methods of the molar absorbance coefficient of the subphthalocyanine derivatives having the phosphorus derivative-substituted group obtained in the Examples 1-9 and the halo boron subphthalocyanine obtained in Synthesis Examples 1-4 were carried out as follows.

10.0 mg of the obtained compound was completely dissolved in 100 ml of chloroform. Then 10 ml of the solution was diluted with 100 ml of chloroform. Thus the absorbance of the obtained solution was measured using spectrophotometer (UV-1700 available from Shimadzu Corporation). Molar absorbance coefficient • was calculated using the following equation:

$$A = \bullet \times C \times l$$

(A: absorbance, C: concentration (mol/L), l: light path (cm))
In the measurement, light pass length of the cell is 1 cm long.

In table 10 shown below, molecular formula, molecular weight, yield, maximum absorption wavelength and molar absorbance coefficient in chloroform of the compound obtained in Examples mentioned above are shown. In addition, as Comparative Examples, molecular formula, molecular weight, yield, maximum absorption wavelength in chloroform and molar absorbance coefficient of the Intermediate Compounds obtained in the Synthesis Examples 1-4 are also shown.

TABLE 10

| Synthesis No. | Compound | Molecular Formula | Molecular Weight | Yield (%) | Maximum Absorption Wavelength (nm) Molar Absorbance Coefficient ($\times 10^{-4}$ Lmol$^{-1}$cm$^{-1}$) |
|---|---|---|---|---|---|
| Ex. 1 | Compound 1 | $C_{36}H_{22}N_6BO_2P$ | 612.2 | 67.4 | 564.0 7.69 |
| Ex. 2 | Compound 3 | $C_{36}H_{22}N_6BO_4P$ | 644.2 | 64.4 | 564.5 6.96 |
| Ex. 3 | Compound 4 | $C_{32}H_{30}N_6BO_4P$ | 604.2 | 34.3 | 562.5 7.78 |
| Comp. Ex. 1 | Intermediate Compound 1 | $C_{24}H_{12}N_6BCl$ | 430.1 | 34.0 | 565.0 5.10 |
| Ex. 4 | Compound 5 | $C_{48}H_{46}N_6BO_2P$ | 766.3 | 23.3 | 570.5 8.74 |
| Ex. 5 | Compound 7 | $C_{44}H_{54}N_6BO_4P$ | 772.4 | 18.8 | 568.0 7.62 |

TABLE 10-continued

| Synthesis No. | Compound | Molecular Formula | Molecular Weight | Yield (%) | Maximum Absorption Wavelength (nm) Molar Absorbance Coefficient ($\times 10^{-4}$ Lmol$^{-1}$cm$^{-1}$) |
|---|---|---|---|---|---|
| Comp. Ex. 2 | Intermediate Compound 2 | $C_{36}H_{36}N_6BCl$ | 598.3 | 23.5 | 570.0 5.10 |
| Ex. 6 | Compound 11 | $C_{51}H_{52}N_6BO_2PS_3$ | 918.3 | 57.6 | 586.0 7.12 |
| Ex. 7 | Compound 13 | $C_{51}H_{52}N_6BO_4PS_3$ | 950.3 | 46.9 | 586.5 8.20 |
| Comp. Ex. 3 | Intermediate Compound 6 | $C_{39}H_{42}N_6BClS_3$ | 736.2 | 44.0 | 587.5 5.82 |
| Ex. 8 | Compound 24 | $C_{54}H_{34}N_6BO_2PS_3$ | 936.2 | 56.0 | 584.5 7.24 |
| Comp. Ex. 4 | Intermediate Compound 11 | $C_{42}H_{24}N_6BClS_3$ | 754.1 | 49.2 | 586.0 7.58 |
| Ex. 9 | Compound 26 | $C_{50}H_{42}N_6BO_4PS_3$ | 928.2 | 40.0 | 584.0 9.95 |

TABLE 11

| Synthesis No. | Compound | Solubility (wt %) (Solvent: Methyl Ethyl Ketone) |
|---|---|---|
| Ex. 1 | Compound 1 | 0.44 |
| Ex. 2 | Compound 3 | 0.34 |
| Ex. 3 | Compound 4 | >10 |
| Comp. Ex. 1 | Intermediate Compound 1 | 0.003 |
| Ex. 4 | Compound 5 | >10 |
| Ex. 5 | Compound 7 | >10 |
| Ex. 6 | Compound 11 | >10 |
| Comp. Ex. 2 | Intermediate Compound 2 | >10 |
| Ex. 7 | Compound 13 | >10 |
| Comp. Ex. 3 | Intermediate Compound 6 | >10 |
| Ex. 8 | Compound 24 | >10 |
| Comp. Ex. 4 | Intermediate Compound 11 | >10 |
| Ex. 9 | Compound 26 | >10 |

Figure 2:
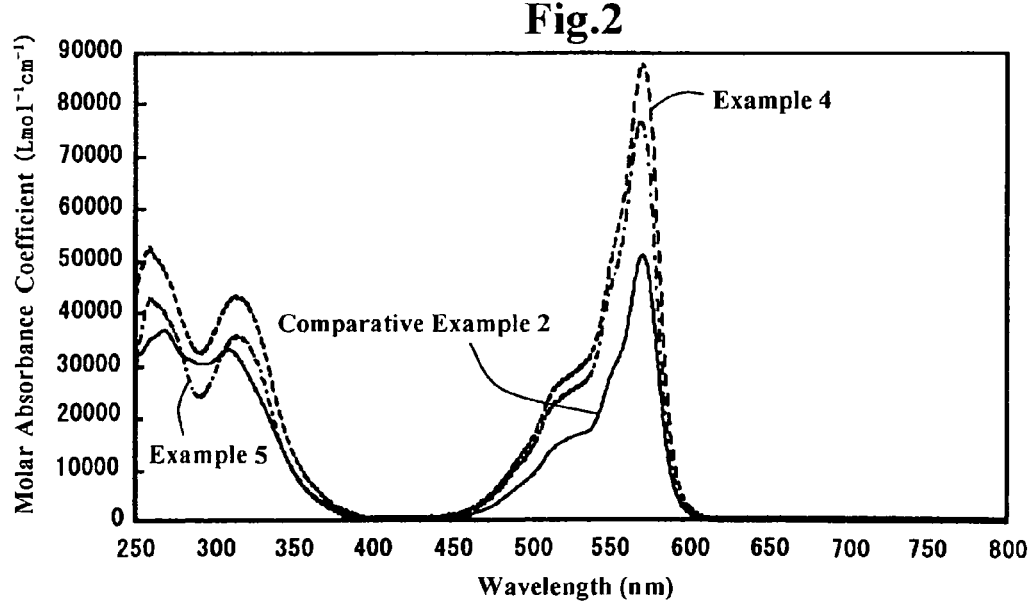
FIG. 2 shows absorption spectra of t-butyl subphthalocyanine derivatives of Examples 4-5 and Comparative Example 2.
Figure 3:
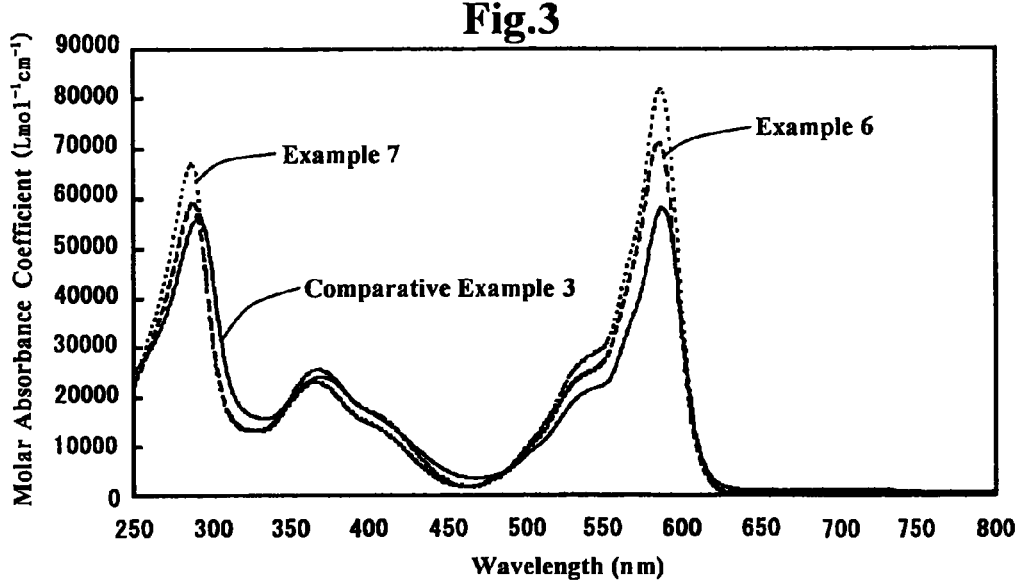
FIG. 3 shows absorption spectra of i-pentylthio subphthalocyanine derivatives of Examples 6-7 and Comparative Example 3.
Figure 4:
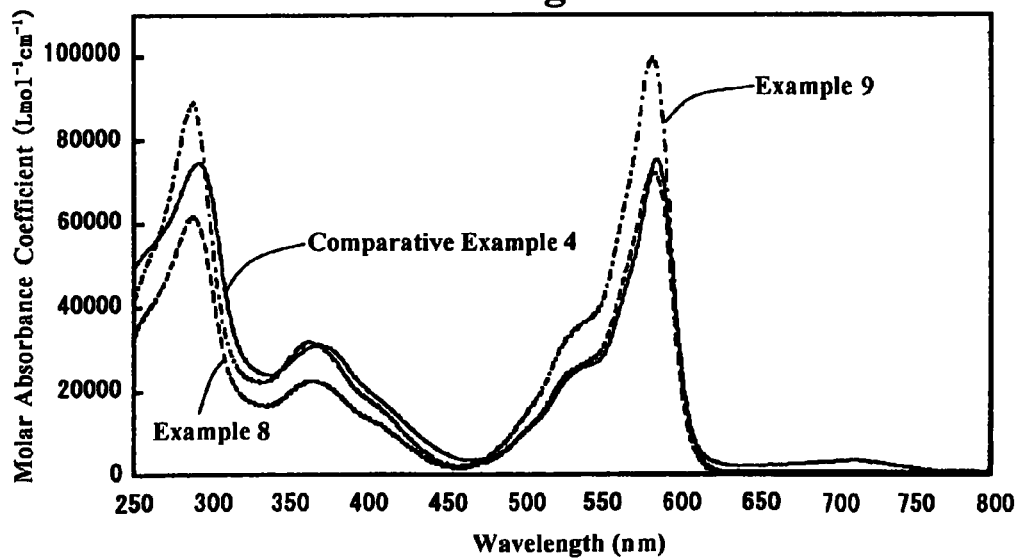
FIG. 4 shows absorption spectra of phenylthio subphthalocyanine derivatives of Examples 8-9 and Comparative Example 4.

Absorption spectra in chloroform of all compounds shown in Table 10 are shown in FIGS. 1 to 4. As shown in FIGS. 1 to 4, almost all of the present subphthalocyanine derivatives having the phosphorus derivative-substituted group have higher molar absorbance coefficient than that of chloro boron subphthalocyanines having the same substituent. And there is almost no shift in Q-band wavelength even though the phosphorus derivative-substituted group is used as the axially substituted group. Solubility of all compounds in Table 10 to methyl ethyl ketone is shown in Table 11. When the Compounds 1, 3 and 4 are compared with Intermediate Compound 1, all of which are derivatives having no peripheral substituent, solubility of the Compound 1, 3 and 4 was remarkably improved due to the introduction of the axially substituted group made of the phosphorus derivative. In particular, Compound 4 demonstrates a high solubility of more than 10% by weight. Further, when compared with Compounds 5-13, the present subphthalocyanine derivatives maintain a high solubility even though the phosphorus derivative is used as the axially substituted group. Accordingly, solubility can be controlled by molecular design based on the effect of the peripheral substituent.

Next, a method for manufacturing thin films of the subphthalocyanine derivatives having the phosphorus derivative-substituted group and a method for evaluating the thin films are explained. In Examples, "parts by weight" is abbreviated as "parts" hereinafter.

Example 10

A thin film containing Compound 1 which is a coloring matter for a thin film obtained in Example 1 of the present invention was produced by a process shown below.

0.5 parts of Compound 1 obtained in Example 1 and 1.0 parts of polycarbonate were added into 68.5 parts of cyclohexanone and 30 parts of methyl ethyl ketone and stirred and dissolved to obtain a coating solution.

The obtained coating solution was applied on a 1 mm-thick glass plate using automatic film applicator (available from Coating Tester Kogyo Corporation) to manufacture a thin film.

Example 11

A film was manufactured in the same way as in Example 10 except that Compound 3 obtained in Example 2 was used in place of Compound 1 in Example 10.

Example 12

A film was manufactured in the same way as in Example 10 except that Compound 4 obtained in Example 3 was used in place of Compound 1 in Example 10.

Example 13

A film was manufactured in the same way as in Example 10 except that Compound 5 obtained in Example 4 was used in place of Compound 1 in Example 10.

Example 14

A film was manufactured in the same way as in Example 10 except that Compound 7 obtained in Example 5 was used in place of Compound 1 in Example 10.

Example 15

A film was manufactured in the same way as in Example 10 except that Compound 11 obtained in Example 6 was used in place of Compound 1 in Example 10.

Example 16

A film was manufactured in the same way as in Example 10 except that Compound 13 obtained in Example 7 was used in place of Compound 1 in Example 10.

Example 17

A film was manufactured in the same way as in Example 10 except that Compound 24 obtained in Example 8 was used in place of compound 1 in Example 10.

Example 18

A film was manufactured in the same way as in Example 10 except that Compound 26 obtained in Example 9 was used in place of Compound 1 in Example 10.

Comparative Example 5

A film was manufactured in the same way as in Example 10 except that Intermediate Compound 1 obtained in Synthesis Example 1 was used in place of Compound 1 in Example 10. In this example, Intermediate Compound 1 could not be fully dissolved so that the coating liquid was dispersion liquid.

Comparative Example 6

A film was manufactured in the same way as in Example 10 except that Intermediate Compound 2 obtained in Synthesis Example 2 was used in place of Compound 1 in Example 10.

Comparative Example 7

A film was manufactured in the same way as in Example 10 except that Intermediate Compound 6 obtained in Synthesis Example 3 was used in place of Compound 1 in Example 10.

Measurement of Haze

Haze values of the thin films were determined using a Haze meter (NDH2000 available from Nippon Denshoku Industries Co., LTD.) Haze value of a thin film (blank film) made only of resin was 0.41. The measured haze values are shown in Table 12. In the Table 12, the symbol of "A" represents a haze value of not more than 1.0, "B" represents not more than 1.5, "C" represents not more than 2.0 and "D" represents not less than 2.0.

Measurement of Heat Resistance

Heat resistance of the thin films containing the present subphthalocyanine derivative of the present invention was evaluated using a heated air oven (WFO-600SD available from EYELA). The thin films were heated at 180° C. for 30 minutes, and then absorbance of the thin films was measured to determine the percentage change in the light absorbance before and after the heat treatment. The results of the heat resistance measurements were shown in Table 12. In the Table 12, the symbol of "A" represents a percentage change of not more than −10%, "B" represents not more than −20%, "C" represents not more than −30% and "D" represents not less than −30%.

Measurement of Light Resistance

Evaluation of the light resistance of specimens of the thin films containing the present subphthalocyanine derivative was carried out by previously putting an ND-10 filter (the transmitted light is 1/10) on the thin films and then leaving the specimens in a xenon fade-o-meter (Ci-4000 available from Atlas Material Testing Technology) at a temperature of 45° C. (BST Temperature) and a relative humidity of 50% under an irradiance of 25 w/m² for 2 hours. Absorbance of the thin films before and after the irradiation was measured, and then the percentage change in absorbance was calculated to estimate the light resistance.

Light resistances are shown in Table 12. In the Table 12, the symbol of "A" represents the percentage change of not more than −20%. "B" represents not more than −30%, "C" represents not more than −40% and "D" represents not less than −50%.

TABLE 12

| Example No. | Haze Value | Rating | Heat Resistance (%) | Rating | Light Resistance (%) | Rating |
|---|---|---|---|---|---|---|
| Ex. 10 | 0.52 | A | −14.1 | B | −32.1 | C |
| Ex. 11 | 0.38 | A | −8.3 | A | −25.8 | B |
| Ex. 12 | 0.43 | A | −9.7 | A | −29.0 | B |
| Comp. Ex. 5 | 9.89 | D | −52.8 | D | No Data | * |
| Ex. 13 | 0.33 | A | −11.8 | B | −32.9 | C |
| Ex. 14 | 0.34 | A | −9.5 | A | −38.6 | C |
| Ex. 15 | 0.31 | A | −17.4 | B | −38.5 | C |
| Comp. Ex. 6 | 0.35 | A | −27.1 | C | −37.1 | C |
| Ex. 16 | 0.37 | A | −14.9 | B | −33.3 | C |
| Comp. Ex. 7 | 0.34 | A | −21.2 | C | −33.6 | C |
| Ex. 17 | 0.32 | A | −7.8 | A | −17.3 | A |
| Ex. 18 | 0.48 | A | −9.4 | A | −15.6 | A |

* Measurement could not be carried out because only unhomogenuous solution was obtained and accordingly non-uniform thin films were obtained.

Regarding the haze value, thin film made of only resin (blank thin film) had a haze value of 0.41. Compared to this value, the thin film of Comparative Example 5 had a poor haze value because the film was made from pigment-dispersed liquid. Other thin films had haze values nearly equal to or less than that of the blank thin film, showing good results.

Regarding the heat resistance, the thin films made of novel subphthalocyanine derivatives having the phosphorus derivative-substituted group of the present invention showed excellent results as a whole when compared to those of Comparative Examples. Regarding the light resistance, nearly equal results to Comparative Examples were seen as a whole but Examples 17 and 18 showed excellent results. Therefore the thin films of the present invention dominate over the films of Comparative Examples.

Industrial Applicability

The subphthalocyanine derivatives having the phosphorus derivative-substituted group of the present invention have high solubility to various solvents and good resistance to heat and light. Accordingly, the optical film containing the present subphthalocyanine derivative has improved toughness. In addition, this optical film has a property to effectively block light that has a narrow and specific absorption wavelength in a range of 510-610 nm and makes an image unclear. Thus, this optical film is highly useful for improving visibility of a display. In addition, half width thereof is comparatively narrow and therefore transmission of red light, whose wavelength is close to the absorbing wavelength, is hardly hampered so that this film can be used for various functional optical thin films.

What is claimed is:

1. A subphthalocyanine derivative having a phosphorus derivative-substituted group, which is represented by the following chemical formula (1):

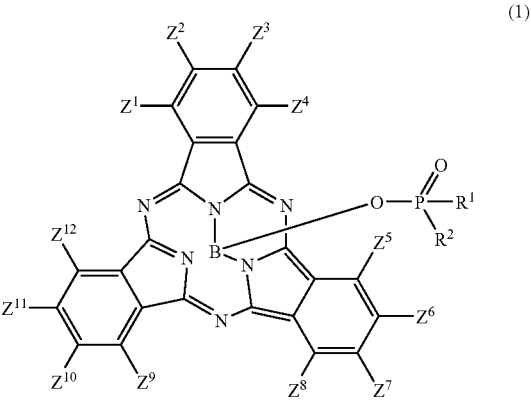

(wherein $Z^1$-$Z^{12}$ are the same or different from each other and each represents a hydrogen atom, a hydroxyl group, a mercapto group, an alkyl containing group, a partial fluoro alkyl containing group, a perfluoro alkyl containing group, an aralkyl containing group, a partial fluoro aralkyl containing group, a perfluoro aralkyl containing group, an aryl group, an amino group, an alkoxyl group or a thioether group, and $R^1$ and $R^2$ are the same or different from each other and each represents an alkyl group, an aralkyl group, a phenyl group, an alkoxyl group or a phenoxy group.)

2. A method for manufacturing a subphthalocyanine derivative having a phosphorus derivative-substituted group, comprising;

a step for reacting a halo boron subphthalocyanine represented by the following chemical formula (2):

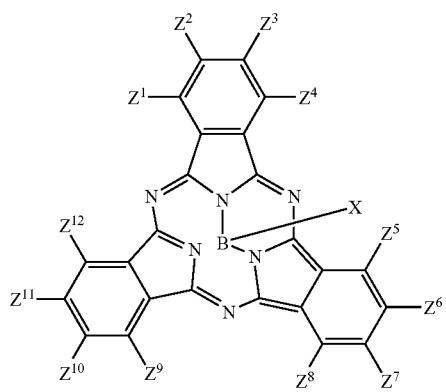

(2)

(wherein $Z^1$-$Z^{12}$ are the same as in the chemical formula (1), X is a halogen atom selected from the group consisting of fluorine, chlorine, bromine and iodine,)

with a compound represented by the following chemical formula (3):

$R^1R^2PO_2H$  (3)

(wherein $R^1$ and $R^2$ are the same or different from each other and are each selected from the group consisting of a straight or branched alkyl group having 1-20 carbon atoms, an aralkyl group, a phenyl group, an alkoxyl group and a phenoxy group, each of which have no substituent or one or more substituents,)

to manufacture a subphthalocyanine derivative having a phosphorus derivative-substituted group, which is represented by the following chemical formula (1):

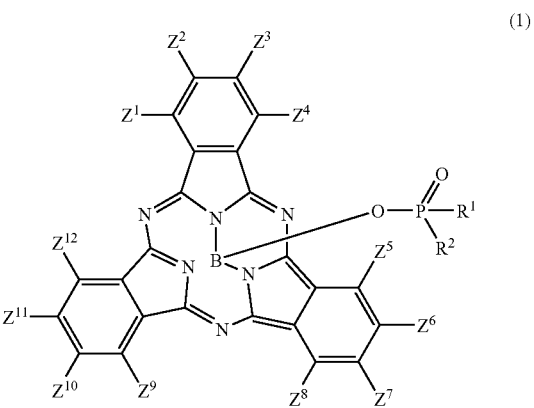

(1)

(wherein $Z^1$-$Z^{12}$, $R^1$ and $R^2$ are the same as described above.)

3. An optical film containing the subphthalocyanine derivative having the phosphorus derivative-substituted group according to claim 1.

* * * * *